United States Patent
DiUbaldi et al.

(10) Patent No.: US 8,260,439 B2
(45) Date of Patent: Sep. 4, 2012

(54) NERVE STIMULATION PATCHES AND METHODS FOR STIMULATING SELECTED NERVES

(75) Inventors: Anthony DiUbaldi, Jackson, NJ (US); Michael Tracey, Branchburg, NJ (US); Rex O. Bare, Lake Forest, CA (US); Bradley Sargent, Mission Viejo, CA (US); Stephen B. Wahlgren, Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 1185 days.

(21) Appl. No.: 11/941,508

(22) Filed: Nov. 16, 2007

(65) Prior Publication Data

US 2009/0132018 A1 May 21, 2009

(51) Int. Cl.
*A61N 1/18* (2006.01)
(52) U.S. Cl. ........................... 607/152; 607/145
(58) Field of Classification Search .................. 607/115, 607/145, 148–150, 152
See application file for complete search history.

(56) References Cited

U.S. PATENT DOCUMENTS

| | | | |
|---|---|---|---|
| 4,406,288 A | 9/1983 | Horwinski | |
| 4,537,195 A | 8/1985 | McDonnell | |
| 4,719,922 A | 1/1988 | Padjen | |
| 4,989,605 A | 2/1991 | Rossen | |
| 5,423,874 A * | 6/1995 | D'Alerta | 607/72 |
| 5,562,717 A | 10/1996 | Tippey | |
| 5,702,428 A | 12/1997 | Tippey | |
| 2003/0233137 A1 | 12/2003 | Paul | |
| 2004/0162602 A1 | 8/2004 | Cohen | |
| 2005/0277998 A1 | 12/2005 | Tracey | |
| 2006/0195153 A1 * | 8/2006 | DiUbaldi et al. | 607/41 |
| 2009/0048563 A1 * | 2/2009 | Ethelfeld et al. | 604/174 |

FOREIGN PATENT DOCUMENTS

| | | |
|---|---|---|
| EP | 0 504 715 A | 9/1992 |
| WO | WO 01/97911 A | 12/2001 |
| WO | WO 2006/113801 A | 10/2006 |

OTHER PUBLICATIONS

International Preliminary Search Report on Patentability for International Application No. PCT/US2008/082435, dated May 18, 2010.

* cited by examiner

*Primary Examiner* — Eric D. Bertram
(74) *Attorney, Agent, or Firm* — Cheryl F. Cohen, LLC

(57) ABSTRACT

A selective nerve stimulation patch includes a substrate having a top surface and a bottom surface, integrated components overlying the top surface of the substrate and being electrically interconnected with one another for generating at least one nerve stimulating signal, electrodes integrated into the substrate and exposed at the bottom surface thereof for applying the at least one nerve stimulating signal to a target nerve, a waterproof, breathable cover overlying the substrate and the integrated components, and a support flange surrounding the substrate and coupling the cover and the substrate together. The support flange has a top surface that slopes downwardly toward an outer perimeter thereof, and at least a portion of the cover conforms to the sloping top surface of the support flange. In one embodiment, the patch generates a high frequency waveform with properties such as amplitude, frequency and the like chosen so as to overcome tissue impedance and the stimulation threshold of the target nerve. The modulated waveform is the waveform obtained by modulating the carrier waveform by a pulse envelope.

22 Claims, 12 Drawing Sheets

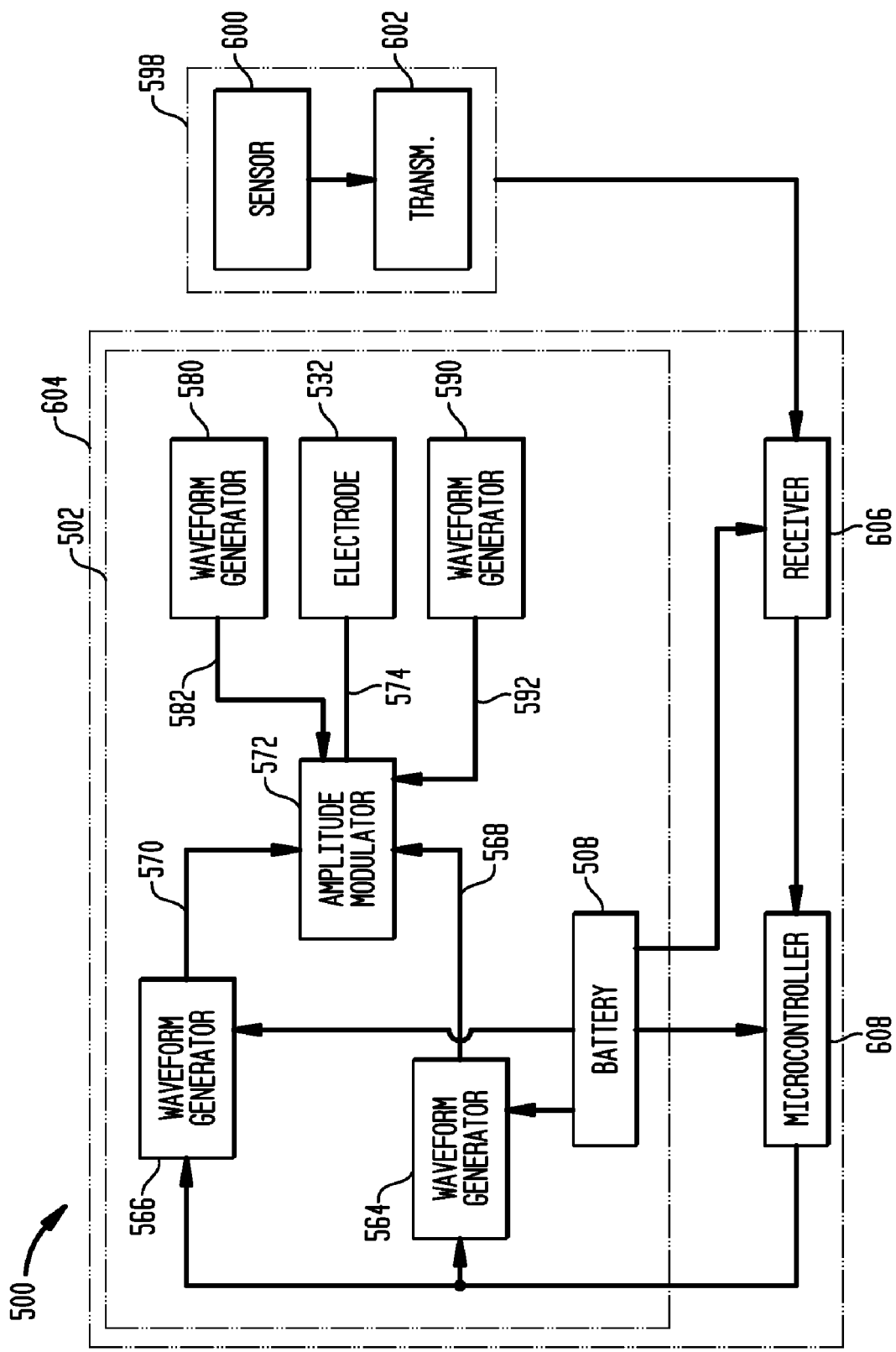

NERVE STIMULATION PATCHES AND METHODS FOR STIMULATING SELECTED NERVES

BACKGROUND OF THE INVENTION

1. Field of the Invention

The present invention is generally related to stimulating nerves and body parts. More specifically, the present invention is related to nerve stimulation patches used for stimulating nerves and body parts to achieve therapeutic results.

2. Description of the Related Art

Nerves are part of the peripheral nervous system of a human body. They convey sensory signals back and forth from the skin and body organs to the central nervous system. Nerves may become damaged due to wear and tear, physical injuries, infection, and/or the failure of the blood vessels surrounding the nerves. These functional defects may be accompanied by pain, numbness, weakness, and in some cases, paralysis. Other problems resulting from damaged nerves may include urinary and fecal incontinence.

Different tactics have been developed to treat the above-mentioned problems. For example, treating urinary incontinence may involve behavior modification such as urinating more frequently and wearing protective undergarments. In certain social situations, however, individuals may not be able to follow the practice of frequent urination or wearing protective undergarments. Another approach involves a medical therapy including taking prescribed drugs. This methodology may result in adverse side effects or drug interactions, however, that will ultimately require discontinuation.

Another technique for treating the above-mentioned conditions involves stimulating a nerve using an electro-medical device that is positioned near a target nerve. One such electro-medical device is commonly referred to as an Implantable Pulse Generator (IPG). An IPG typically includes one or more electrodes, an electrical pulse generator, a battery, and a housing. The electrical pulse generator generates an electrical signal adapted to stimulate a target nerve. When the electrodes receive the signal from the generator, they draw energy from the battery and generate an electric field of suitable strength to stimulate the target nerve.

IPG's have proven to be somewhat effective for stimulating nerves, however, they are extremely invasive because they must be implanted inside a patient's body during a surgical procedure. IPG's also consume a significant amount of power, which may be due to an increase in electrical impedance between the electrodes, or an increase in electrical impedance between the electrodes and the IPG. This may happen due to several factors such as electrode migration, encapsulation of one or more electrodes, and material property changes in the electrodes or body tissue. Material property changes in the electrodes may occur due to a number of factors including chemical changes caused by body fluids being present at the surface of the electrodes, frequent passing of electrical current through the tissue, and normal wear and tear occurring during daily activities.

Higher battery power consumption may also be caused by a phenomenon referred to as "desensitization of stimulus," whereby the human body responds to an applied external charge by offering a resistance to the applied external charge. The body resists the applied external charge by increasing the stimulation threshold for a target nerve, thereby rendering the earlier stimulus level ineffective. To overcome this problem, a more powerful charge must be generated, which consumes even more battery power. This requires frequent replacement and/or recharging of the batteries.

In some nerve stimulation devices, it has been observed that the generated electric field spreads widely, affecting untargeted muscles and nerves along with the target nerve. The wide spreading of the electric field significantly reduces the strength of the electrical signal at the target nerve. In order to properly stimulate the target nerve, the strength of the electrical signal must be substantially increased. This requires the devices to draw more power from the battery.

There have been a number of efforts seeking to stimulate nerves in a more efficacious and non-invasive manner. For example, non-invasive techniques for treating the above conditions are disclosed in commonly assigned U.S. Patent Publication Nos. 2005/0277998, filed Jun. 7, 2005, and US 2006/0195153, filed Jan. 31, 2006, the disclosures of which are hereby incorporated by reference herein. Specifically, in one or more embodiments thereof, the '998 publication teaches a non-invasive, transcutaneous neurostimulation device that generates and transmits a controlled, amplitude-modulated waveform comprising a carrier signal and a pulse envelope. The carrier waveform is designed to be of sufficient frequency to overcome attenuation due to tissue impedances. The pulse envelope contains specific pulse width, amplitude and shape information designed to stimulate specific nerves.

FIGS. 1 and 2 show a conventional nerve stimulating device 20 including a first layer 22 having a top surface 24 and a bottom surface 26. The bottom surface 26 of the first layer 22 is covered by an adhesive layer 28 having openings 30A, 30B extending therethrough that accommodate active and return integrated electrodes 32A, 32B. The adhesive layer 28 includes the holes that accommodate the shape of the electrodes 32A, 32B and allow direct contact of the electrodes with the surface of a patient's skin. The device 20 includes electrolyte pads 34A, 34B that cover the respective electrodes 32A, 32B. The electrodes 32A, 32B may be secured directly to the first layer 22, or may be held in place by a second layer comprised of any suitable material such as a plastic. The integrated electrodes may be gold-plated or other corrosion-resistant electro-deposited metal pads for the connection to the electrolyte for the stimulating electrode. The device includes a third layer 36 of a flexible electronics board or flex board that contains all of the electronic elements described in the '998 publication and that is electrically coupled to the electrodes 32A, 32B. The flex board 36 has parts that are folded over the batteries to complete battery connections and to nest the electronic components into a more compact space. A fourth layer is a thin film battery 38 of any suitable size and shape that can be held in place by a battery seal or ring 40, and the top cover 42 is any suitable covering such as the plastic coverings commonly used in bandages.

Referring to FIG. 2, the nerve stimulating device 20 includes a photodiode 44 underlying a section of the top layer, which can be used as an extremely low-power communication receiver. The photodiode is small, inexpensive, consumes zero power when inactive, and is much more energy and space-efficient than an RE link. The device 20 includes electrodes 32A, 32B powered by batteries 38A, 38B, which are surrounded by battery seals 40A, 40B. The two stimulation electrodes 32A, 32B are shifted off to one side, resulting in a somewhat D-shaped device. The top cover 42 is water resistant for protecting the internal components during typical activities such as washing, bathing and showering.

In spite of the above advances, there remains a need for improved devices and methods of stimulating body parts and nerves. In particular, there remains a need for selective nerve stimulation patches that are more compact and have a smaller footprint, that are more economical, that have less parts, and that are easier to assemble. There also remains a need for improved nerve stimulation devices that effectively stimulate target nerves and body parts, while not stimulating untargeted nerves and body parts. Furthermore, there remains a need for nerve stimulation devices that are less invasive, and that require less power to operate effectively, thereby minimizing the need to replace and/or recharge power sources.

SUMMARY OF THE INVENTION

The present invention relates to systems, devices and methods for stimulating nerves and body parts. In one embodiment, a compact selective nerve stimulation patch generates and applies nerve stimulating signals that effectively pass through the body for stimulating target nerves and body parts. In one embodiment, the nerve stimulating signals are waveforms that may be modulated for enhancing the efficiency of the waveforms passing through the body. The efficiency results in a device that stimulates target nerves while not stimulating untargeted nerves, that consumes less battery power, and that can operate for a longer period of time before being recharged.

In one embodiment of the present invention, a nerve stimulation patch includes a substrate, such as a circuitized substrate, having a top surface and a bottom surface, components, such as active and passive components, overlying the top surface of the substrate and being electrically interconnected with one another for generating at least one nerve stimulating signal, and at least one electrode disposed on the substrate and exposed at the bottom surface thereof for applying the at least nerve stimulating signal. The nerve stimulation patch desirably includes a waterproof, breathable top cover overlying the substrate, such as a material sold under the trademark GORE-TEX, and a support flange surrounding the substrate and coupling the top cover with the substrate.

In one embodiment of the present invention, the support flange has a top surface that slopes downwardly toward an outer perimeter of the support flange, and a portion of the top cover conforms to the top surface of the support flange. The support flange may include vent openings extending from an underside thereof to the top surface thereof. The vent openings are desirably in communication with the top cover for venting moisture from inside the patch to outside the patch.

In one embodiment of the present invention, the nerve stimulation patch includes an encapsulant at least partially covering the components on the substrate and the top surface of the substrate, whereby the support flange surrounds the encapsulant. In one embodiment, the encapsulant is transparent so that light can pass into and out of the encapsulant layer. At least a portion of the top cover overlying the encapsulant may be at least partially translucent, at least partially transparent, or transparent.

In one embodiment of the present invention, the components overlying the substrate include a power source, such as a battery, and a switch coupled with the power source for activating the patch. The switch may be a single-use switch that is adapted to be activated only one-time. The components may also include a light emitting element, such as an LED, for generating light signals indicating that the patch is activated, and an optical sensor, such as a photodiode, adapted to receive signals for controlling parameters associated with the at least one nerve stimulating signal. In one embodiment, light signals are directed at the photodiode, and the sense light signals are used to adjust the nerve stimulating output of the patch.

In one embodiment of the present invention, a nerve stimulation patch includes a circuitized substrate having a top surface and a bottom surface, a plurality of integrated components overlying the top surface of the circuitized substrate for generating at least one nerve stimulating signal, a power source overlying the top surface of the circuitized substrate for energizing the integrated components, and electrodes disposed within the circuitized substrate. The electrodes are accessible at the bottom surface of the circuitized substrate, and are electrically interconnected with the integrated components for applying the at least one nerve stimulating signal. The selective nerve stimulation patch desirably includes a waterproof, breathable cover overlying the circuitized substrate, and a support flange coupled with and surrounding the circuitized substrate, the support flange having a top surface that slopes downwardly toward an outer perimeter thereof. The support flange may be flexible and may have a plurality of vent openings accessible at the sloping top surface thereof that are in communication with the waterproof, breathable top cover for venting moisture from the patch.

In one embodiment, the nerve stimulation patch includes conductive, adhesive pads, such as adhesive hydrogel pads, overlying the electrodes for securing the patch to a surface. The conductive, adhesive pads are replaceable, which enables the patch to be temporarily removed from a surface and then replaced or re-positioned on the surface.

In one embodiment of the present invention, a nerve stimulation patch includes a substrate having a top surface and a bottom surface, integrated components overlying the top surface of the substrate and being electrically interconnected with one another for generating at least one nerve stimulating signal, and electrodes integrated into the substrate and being exposed at the bottom surface thereof for applying the at least one nerve stimulating signal. The patch desirably includes a waterproof, breathable cover overlying the substrate and the integrated components, and a support flange surrounding the substrate and coupling the waterproof, breathable cover with the substrate. The support flange preferably has a top surface that slopes downwardly toward an outer perimeter thereof, whereby at least a portion of the cover conforms to the sloping top surface of the support flange.

In one embodiment of the present invention, a transparent encapsulant material overlies the integrated components, and the support flange surrounds the transparent encapsulant. The integrated components may include a power source, a one-time activation switch, a light emitting element, and an optical sensor. In one embodiment, the waterproof, breathable cover has a first opening aligned with the one-time activation switch, a second opening aligned with the light emitting element, and a third opening aligned with the optical sensor. The patch may include conductive, adhesive pads covering the electrodes, and an adhesive layer covering a peripheral, underside portion of the waterproof, breathable cover for attaching the patch to a surface. The adhesive pads and the adhesive layer may enable the patch to be temporarily removed from a surface, and then later re-attached to the surface. In one embodiment, the adhesive pads may be replaced with new adhesive pads.

Although the present invention is not limited by any particular theory of operation, it is believed that integrating the electrodes into a substrate, minimizes the size and footprint of the nerve stimulation patch. As a result, the nerve stimulation patch will have a lower overall profile and a smaller footprint over a surface, such as a patient's skin surface.

In one embodiment of the present invention, the selective nerve stimulation patch may include one or more electrodes, one or more waveform generators, one or more modulators, and a battery. The waveform generators preferably generate waveforms capable of selectively stimulating target nerves and penetrating the tissues between the patch and the target nerves. A battery is a preferred power source for the nerve stimulation patch, and the waveform generators draw power from the battery. The modulator modulates the waveforms from the waveform generator to produce a modulated waveform, and sends it to the electrodes. Upon receiving the electrical signals from the modulator, the electrodes desirably generate an electric field for stimulating the target nerve.

In one embodiment of the present invention, the battery is a non-rechargeable battery. In another embodiment of the present invention, the battery is a rechargeable battery, which may be recharged using a radio frequency signal, by using inductive coupling to transfer energy through a shared magnetic field, or by using any other known technique for recharging power sources.

Although the present invention is not limited by any particular theory of operation, it is believed that each nerve has unique physical properties that are attributable to neurons, which are the building blocks of the nerve. The physical properties of a neuron, such as diameter, length, and myelination, determine capacitance and conduction velocity of electrical signals in the nerve. Thus, each nerve can be selectively stimulated by applying a waveform having a particular frequency.

Typically, the excitation frequency of the target nerve lies in the range of 10-40 Hz. The electrical signals with such a low frequency cannot overcome the tissue impedance offered by the tissues between the electrodes and the target nerve that may be caused by encapsulation of the electrodes, or electrode migration over time. The selective nerve stimulation patch of the present invention transmits a controlled, amplitude-modulated waveform composed of a carrier signal and a pulse envelope. The carrier waveform is designed to be of sufficient frequency to overcome tissue impedances. The pulse envelope contains specific pulse width, amplitude and shape information designed to stimulate specific nerves. The high frequency carrier signal can be used to pass through high impedance tissue (subcutaneous or transcutaneous) while the modulating signal is used to activate nervous tissue.

In one or more embodiments of the present invention, the selective nerve stimulation patch is adapted to generate a modulated waveform for stimulating a target nerve using the devices and techniques described in commonly assigned United States Patent Application Publication Nos. US 2005/0277998 (U.S. application Ser. No. 11/146,522, filed Jun. 7, 2005), and US 2006/0195153 (U.S. application Ser. No. 11/343,627, filed Jan. 31, 2006), the disclosures of which are hereby incorporated by reference herein. The waveform is desirably generated by modulating a carrier waveform with a pulse envelope. Properties of the carrier waveform such as amplitude, frequency, and the like, are chosen so as to overcome the tissue impedance and the stimulation threshold of the target nerve. The pulse envelope is a waveform having a specific pulse width, amplitude and shape designed to selectively stimulate the target nerve. This waveform is able to penetrate efficiently through the tissue to reach the target nerve with minimal loss in the strength of the electrical signal, thereby saving battery power that would otherwise have been used in several attempts to stimulate the target nerve with low frequency signals. Moreover, only the target nerve is stimulated, and non-target nerves are not stimulated.

In one embodiment, a selective nerve stimulation patch for stimulating nerves or body parts includes a first waveform generator adapted to generate a first waveform having a first frequency, a second waveform generator adapted to generate a carrier waveform having a second frequency that is higher than the first frequency, a modulator electrically coupled to the first and second waveform generators and adapted to modulate the first waveform and the carrier waveform to generate a modulated waveform, and an electrode electrically coupled to the modulator for applying the modulated waveform. The patch includes a power source, such as a battery, for providing power to the waveform generators and the modulator. In one embodiment, the first and second waveform generators, the modulator, the battery, and the electrodes are all provided on a single substrate such as a circuitized substrate. In one preferred embodiment, the first waveform has a frequency adapted to stimulate a target nerve or a target body part. The first waveform may have a frequency substantially within the range of 10-40 Hz, and the carrier waveform may have a frequency substantially within the range of 10-400 KHz.

In one preferred embodiment, the selective nerve stimulation patch may include a microprocessor adapted to receive biofeedback data, and to control operation of the first and second waveform generators in response to the biofeedback data. The patch also desirably includes a receiving device adapted to receive the biofeedback data, the receiving device being in communication with the microprocessor for providing the biofeedback data thereto. The nerve stimulation patch may also include at least one sensor in communication with the receiving device, whereby the at least one sensor is adapted to sense one or more physiological conditions of a mammal, such as bladder pressure. A transmitter may be coupled with the at least one sensor for transmitting the one or more sensed physiological conditions. The transmitter may be a wireless transmitter.

Although one or more embodiments of the present invention are described in relation to nerve stimulation in females and the female urinary system, it is to be understood that the present invention may be readily adapted for nerve stimulation in males, children, and adults, and use in the urinary system or males, children, and adults. Further, the inventive principles, apparatus and methods disclosed herein may also have application to assessing and treating functionality in other areas, such as coronary or pulmonary functionality. Still further, the inventive principles, apparatus and methods disclosed herein may have application for stimulating various other nerves, such as stimulation of nerves during labor and delivery, or selectively stimulating branches of a given nerve bundle to selectively address different patient conditions. In addition, the technology described herein can be applied to various components of the nervous system that contribute or affect the following conditions: stress urinary incontinence, anal and fecal incontinence, sexual dysfunction, interstitial cystitis, chronic pain such as but not limited to pelvic pain, nocturia, and gastrointestinal disorders such as but not limited to gastric pacing. Moreover, the present invention may be used to stimulate body parts other than nerves, such as glands that secrete hormones, and large muscle groups, such as biceps muscle stimulation associate with physical therapy.

These and other preferred embodiments of the present invention will be described in more detail below.

BRIEF DESCRIPTION OF THE DRAWING

So the manner in which the above recited features of the present invention can be understood in detail, a more particular description of embodiments of the present invention, briefly summarized above, may be had by reference to embodiments, which are illustrated in the appended drawings. It is to be noted, however, the appended drawings illustrate only typical embodiments encompassed within the scope of the present invention. Thus, the drawings are not to be considered limiting, for the present invention may admit to other equally effective embodiments, wherein:

FIG. 17 shows a nerve stimulation patch, in accordance with a further embodiment of the present invention.

DETAILED DESCRIPTION

Figure 1:
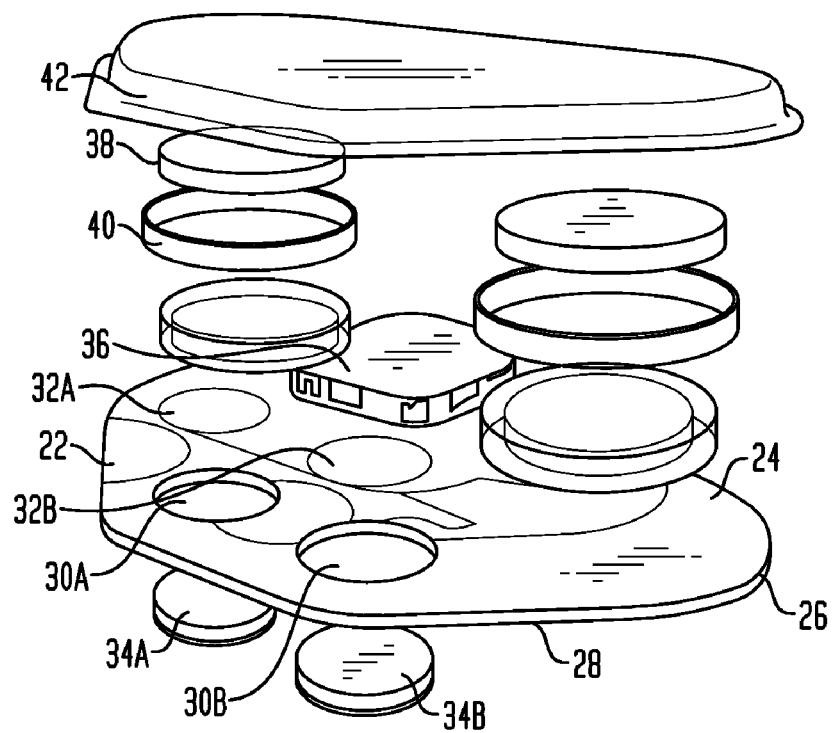
FIG. 1 shows an exploded view of a conventional nerve stimulation patch.

The invention disclosed herein is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although one embodiment of the present invention is described in relation to nerve stimulation in females, it is to be understood that it can be readily adapted for use in males, and children. The inventive principles, apparatus and methods disclosed herein may also have application for stimulating various other nerves, either independently or simultaneously, such as stimulation of nerves during labor and delivery, or selectively stimulating branches of a given nerve bundle to selectively address different patient conditions. Thus, the present invention can, for example, be used to selectively treat or affect one or more of the following conditions simultaneously: stress urinary incontinence, anal and fecal incontinence, pain, sexual dysfunction, interstitial cystitis, chronic pain such as but not limited to pelvic pain, nocturia, and gastrointestinal disorders such as but not limited to gastric pacing. Finally, the present invention as described herein can also be used to stimulate body parts other than nerves, such as glands that secrete hormones, and large muscle groups, such as biceps muscle stimulation associated with physical therapy.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Figure 3:
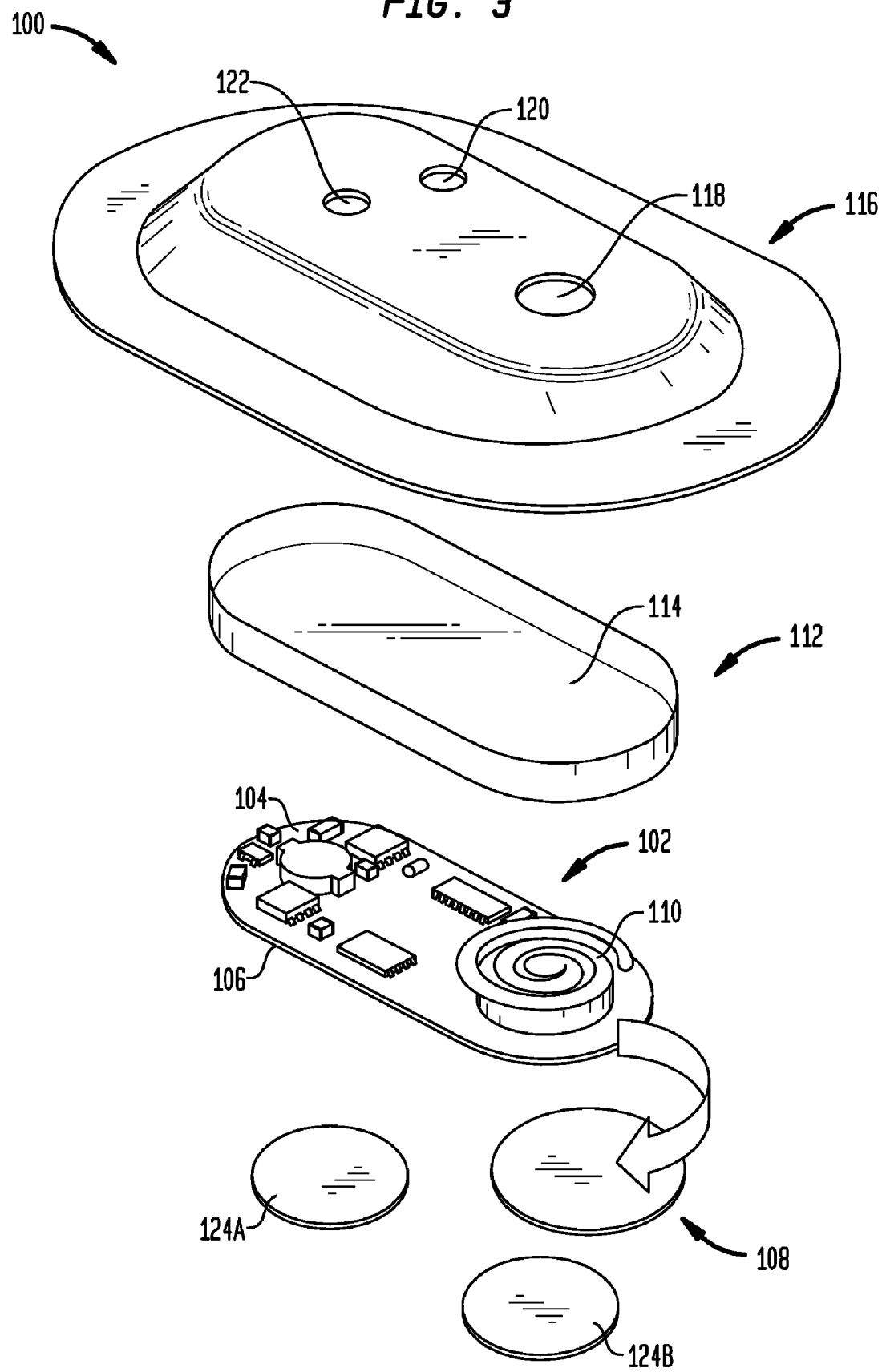
FIG. 3 shows an exploded view of a selective nerve stimulation patch including a substrate, a molded cover, and a waterproof, breathable top cover, in accordance with one embodiment of the present invention.

Referring to FIG. 3, in one embodiment of the present invention, a selective nerve stimulation patch 100 includes a substrate 102, such as a circuitized substrate, having a top surface 104 and a bottom surface 106. The circuitized substrate 102 has components mounted thereon that are adapted to generate electrical signals that may be applied to a body to stimulate one or more selected nerves. In one embodiment, the circuitized substrate 102 has active and passive components that generate electrical signals, modulate the signals and apply the signals to a body for stimulating selected nerves.

The selective nerve stimulation patch 100 includes a power source 108, such as a battery, that provides a source of energy for the patch. In one embodiment, the power source 108 is preferably secured over the top surface 104 of the substrate, and underlies a conductor 110. The patch 100 desirably includes a conductive adhesive (not shown) provided between the conductor 110 and the top surface of the power source 108. In one embodiment, the conductor 110 is part of a single-use or one-time use switch that when activated, permanently connects the power source 108 to the components on the circuitized substrate 102. Initially, the conductor 110 is preferably spaced and isolated from the power source 108. When the conductor 110 is squeezed toward the top surface of the power source, the conductor adheres to the power source (via the conductive adhesive) to provide power for the circuitized substrate and the components attached to the circuitized substrate. The conductor 110 is preferably flexible. In one embodiment, the conductor is a spiral conductor.

The selective nerve stimulation patch 100 preferably includes a molded top cap 112 that is assembled over the circuitized substrate 102. The molded top cap 112 is preferably transparent so that optical signals can pass through the molded top cap, as will be described in more detail below. One end of the molded top cap 112 desirably has a weakened region 114 formed therein that is depressible for pressing the conductor 110 against the top of the battery 108. In other embodiments, the molded top cap 112 may have a uniform thickness throughout the length of the top cap. The molded top cap 112 preferably conforms to the shape of the underlying circuitized substrate 102. In one embodiment, the top cap 112 is formed atop the substrate 102 using injection molding techniques. The molded top cap may comprise an encapsulant material that is curable. In another embodiment, the molded top cap 112 may be formed as a separate part that is assembled with the circuitized substrate.

Referring to FIG. 3, the selective nerve stimulation patch 100 also has a top cover 116 overlying the top cap 112 and the circuitized substrate 102. In one embodiment, the top cover 116 is made of a waterproof, breathable material, such as the material sold under the trademark GORE-TEX. The top cover 116 desirably has a first opening 118 aligned with the conductor 110, a second opening 120 aligned with a LED provided on the substrate, and a third opening 122 aligned with an optical switch such as a photodiode for adjusting the parameters of an output signal or waveform generated by the patch 100.

The selective nerve stimulation patch 100 also includes electrodes (not shown) accessible at the bottom surface 106 of the circuitized substrate 102, and adhesive, conductive pads 124A, 124B that overlie the respective electrodes. In one embodiment, the electrodes are disposed with the substrate and are accessible at the bottom surface of the substrate.

Figure 4:
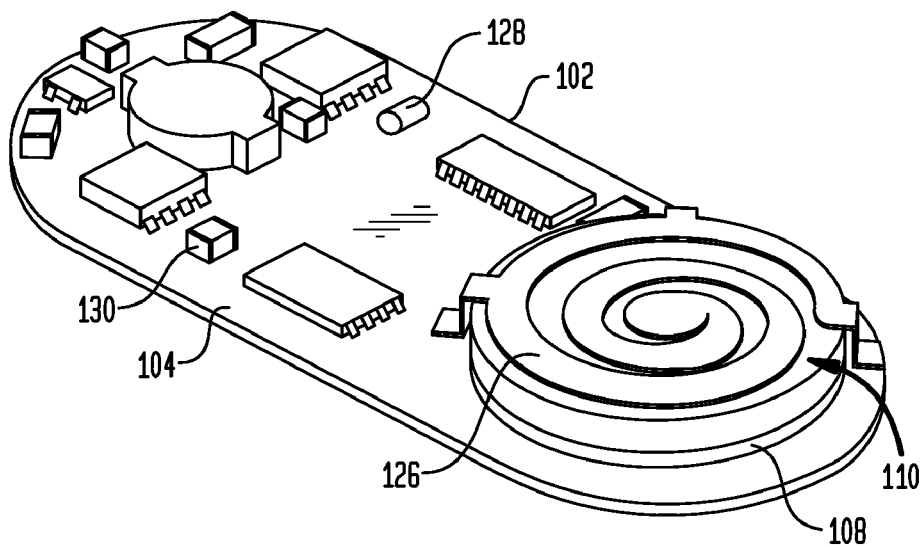
FIG. 4 shows a top perspective view of the substrate shown in FIG. 3.
Figure 5:
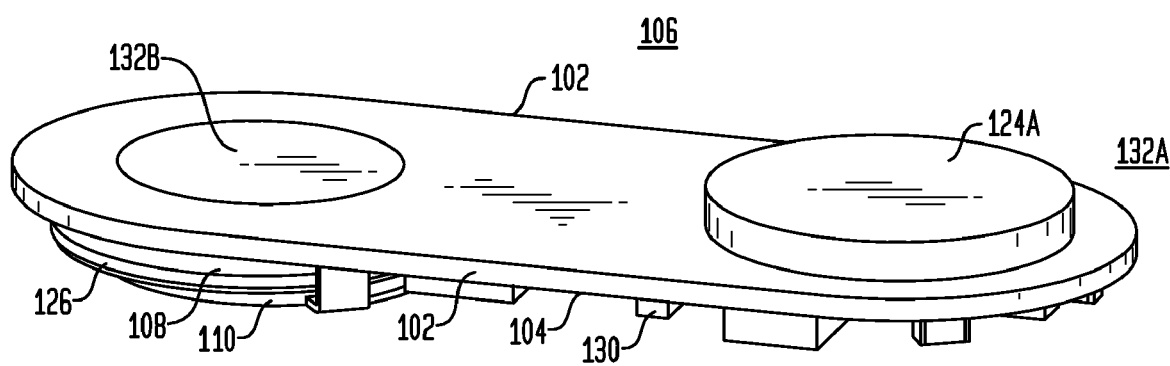
FIG. 5 shows a front elevational view of the substrate of FIG. 3 with the bottom surface of the substrate facing upwardly.

Referring to FIGS. 4 and 5, in one embodiment of the present invention, the circuitized substrate 102 includes the top surface 104 and the bottom surface 106. A power source 108, such as a battery, is positioned over the top surface 104 and under conductor 110. A conductive adhesive 126 is provided between the conductor 110 and the top surface of the battery 108. When the conductor 110 is pressed downwardly toward the top surface of the battery 108, the circuitized substrate is activated or "turned on." The conductive adhesive preferably maintains a permanent electrical interconnection between the conductor 110 and the battery 108 so that the selective nerve stimulation patch remains activated at all times.

Referring to FIG. 4, the circuitized substrate preferably has a light emitting diode (LED) 128 overlying the top surface 104. When the circuitized substrate 102 is activated, the LED 128 emits light that indicates that the patch is operating. The light emitted by the LED 128 may produce a constant stream of light or an intermittent stream of light. The circuitized substrate 102 also has an optical sensor 130 overlying a top surface 104 thereof. The optical sensor 130, such as a photodiode, is responsive to incoming optical signals for adjusting the output waveform or signals generated by the nerve stimulating patch.

Figure 2:
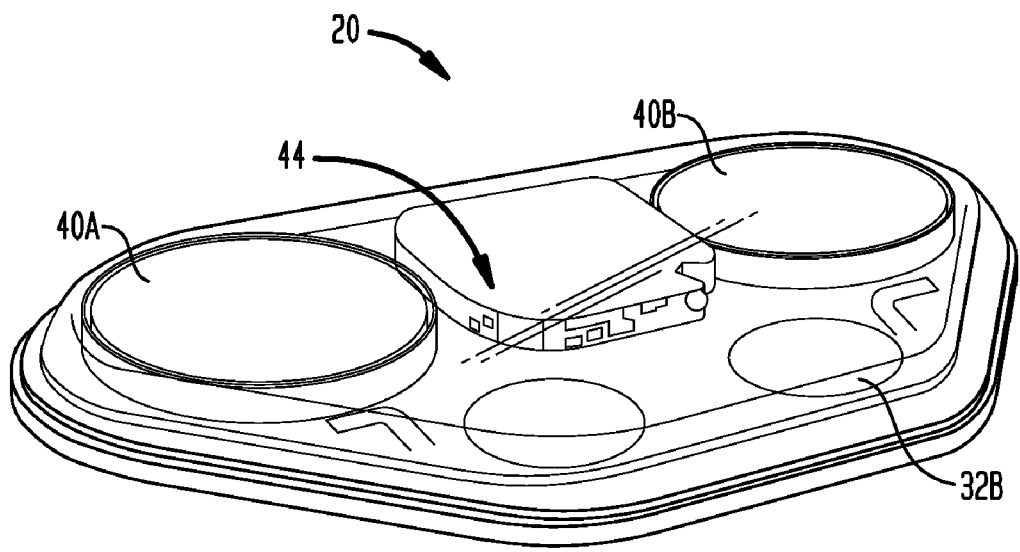
FIG. 2 shows the nerve stimulation patch of FIG. 1 after assembly.

Referring to FIG. 5, in one embodiment of the present invention, the circuitized substrate 102 includes a pair of electrodes 132A, 132B accessible at the bottom surface 106 thereof. The electrodes are desirably integrated into the circuitized substrate for reducing the size of the stimulation patch. In prior art patches, such as the patch shown in FIGS. 1 and 2, the electrodes are spaced from the circuitized substrate, which increases the overall size and footprint of the patch. The present invention seeks to minimize the size and footprint of the patch by integrating the electrodes 132A, 132B into the circuitized substrate and having the electrodes accessible at the bottom surface 106 of the substrate 102. In FIG. 5, an adhesive, conductive pad 124A overlies the first electrode 132A. As will be described in more detail below, the adhesive, conductive pads may be adhesive hydrogel pads, and are adapted to form reliable electrical signal paths between the electrodes 132A, 132B and a patient's skin.

Figure 6:
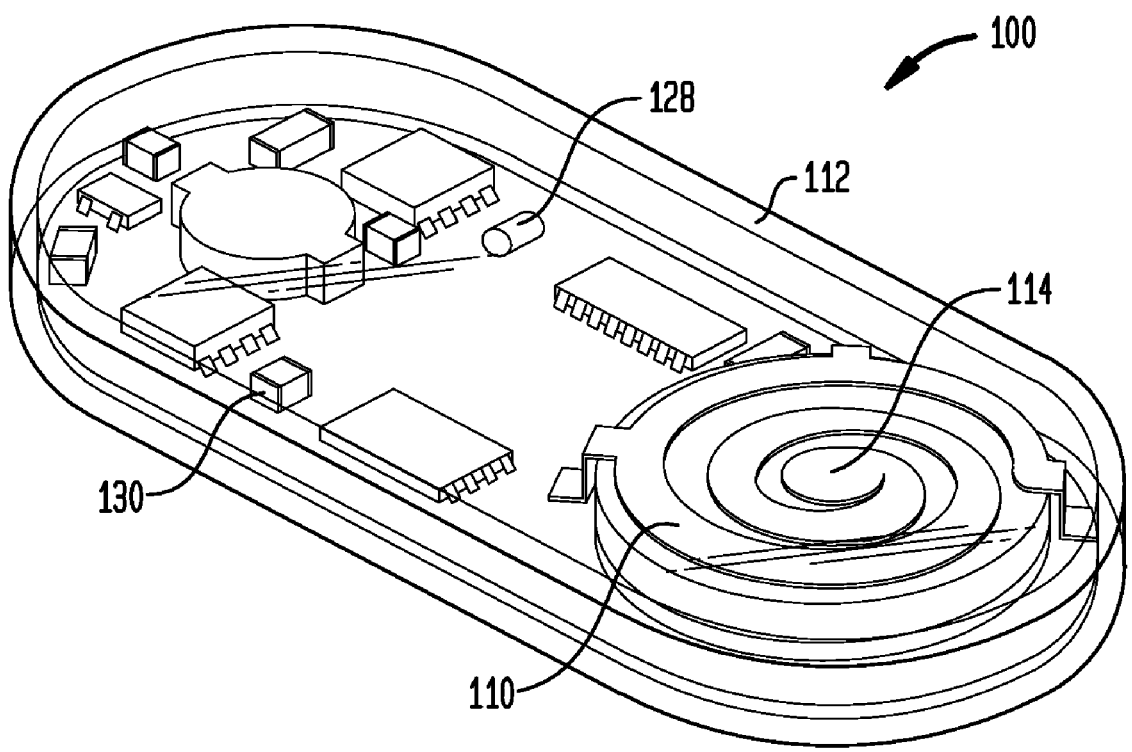
FIG. 6 shows a top plan view of the substrate and molded cover shown in FIG. 3 after the parts have been assembled together, in accordance with one embodiment of the present invention.

Referring to FIG. 6, in one embodiment of the present invention, the molded top cap 112 overlies the circuitized substrate 102 for protecting the components attached to the substrate. The molded top cap 112 is preferably transparent so that light signals can pass therethrough. In one embodiment, the light generated by the LED 128 can pass through the transparent top cap 112 so that the activation status of the patch 100 can be observed. In addition, light signals may be transmitted through the transparent top cap 112 to the optical element 130 for adjusting the waveforms or signals generated by the components attached to the circuitized substrate 102. The molded top cap 112 can be formed in situ atop the substrate 102, or may be formed away from the substrate and then assembled with the substrate 102. In one embodiment, the molded top cap 112 has a thinner or weakened area 114 that is aligned over the conductor 110. The weakened area 114 may be depressed for pressing the conductor 110 against the top of the battery 108 for activating the selective nerve stimulation patch 100.

Figure 7A:
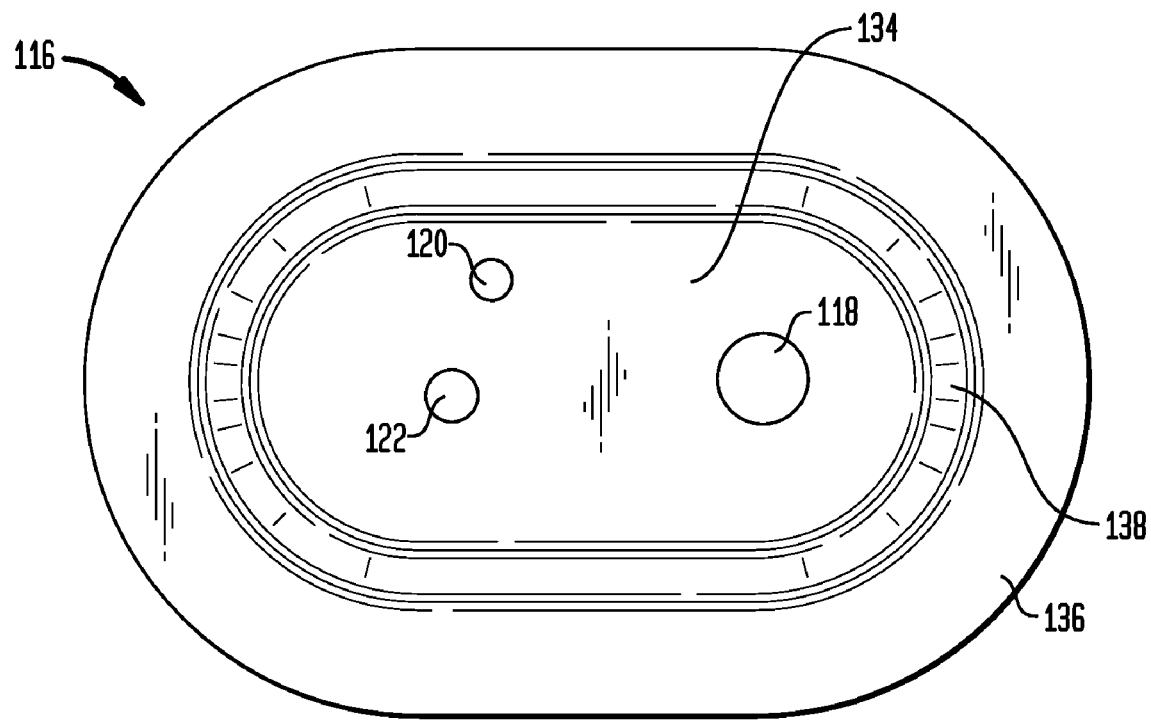
FIG. 7A shows a top plan view of the waterproof, breathable top cover shown in FIG. 3.
Figure 7B:
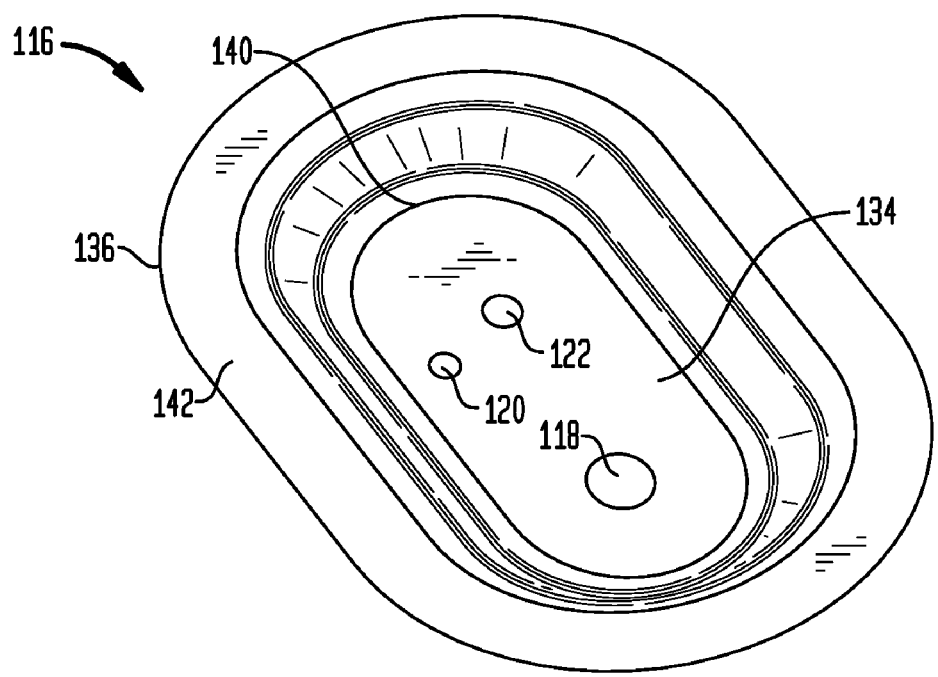
FIG. 7B shows an underside view of the top cover shown in FIG. 7A.

Referring to FIGS. 7A and 7B, in one embodiment of the present invention, the selective nerve stimulation patch includes a top cover 116 that overlies the circuitized substrate and the molded top cap. The top cover 116 is preferably made of a flexible, waterproof, breathable material such as the material sold under the trademark GORE-TEX. As is well-known to those skilled in the art, GORE-TEX material is made of a thin, porous fluoropolymer membrane with a urethane coating that is bonded to a fabric, usually nylon or polyester. The membrane has about 9 billion pores per square inch, each of which is approximately 20,000 times smaller than a water droplet, making it impenetrable to liquid water while still allowing smaller sized water vapor to pass through. As a result, GORE-TEX is a material that is breathable, waterproof, and also windproof. The outer fabric may be treated with water repellent. Seams may be sealed to prevent water leakage through pinholes caused during the sewing of the fabric. The urethane coating provides a protective layer and also prevents contamination (i.e. body oils) from wetting the laminate and allowing wicking of moisture through the membrane. Thus, the top cover 116 prevents water from entering the patch while allowing water vapor and moisture to escape from the patch. In one embodiment, the top cover 116 has a central, raised plateau 134, a substantially flat outer edge 136 that surrounds the central plateau 134, and a sloped transition region 138 that extends between the central plateau 134 and the outer edge 136. In one embodiment, the central plateau 134 has one or more opening extending therethrough. A first opening 118 is preferably aligned with the flexible conductor overlying the battery, a second opening 120 is preferably aligned with the LED, and a third opening 122 is preferably aligned with the optical sensor such as a photodiode.

Referring to FIG. 7B, in one embodiment of the present invention, the underside of the top cover 116 has one or more adhesive layers provided thereon. In FIG. 7B, a first adhesive layer 140 covers the underside of the central plateau 134, and has opening extending therethrough that are in substantial alignment with the openings 118, 120, 122 formed in the top cover 116. A second adhesive layer 142 covers the underside, peripheral edge 136 of the top cover 116. The first adhesive layer 140 preferably adheres the top cover 116 to the top cap overlying the circuitized substrate, and the second adhesive layer 140 preferably adheres the top cover 116 to a surface such as a patient's skin surface.

Figure 8A:
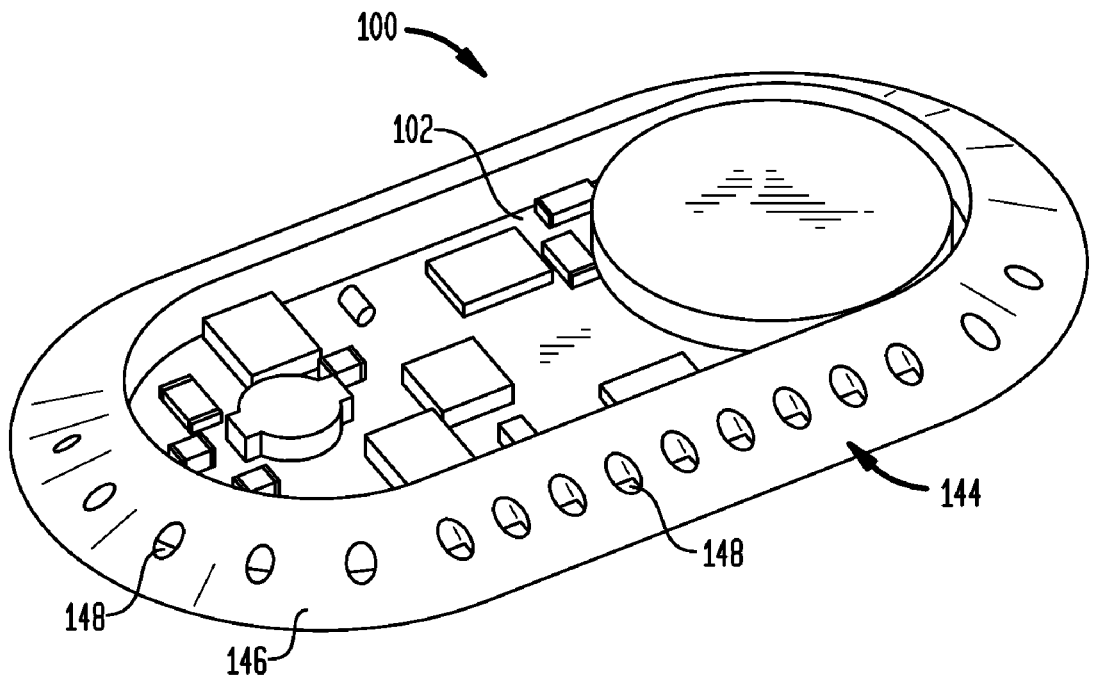
FIG. 8A shows a perspective view of a nerve stimulation patch including a substrate and a support flange surrounding the substrate, in accordance with one embodiment of the present invention.
Figure 8B:
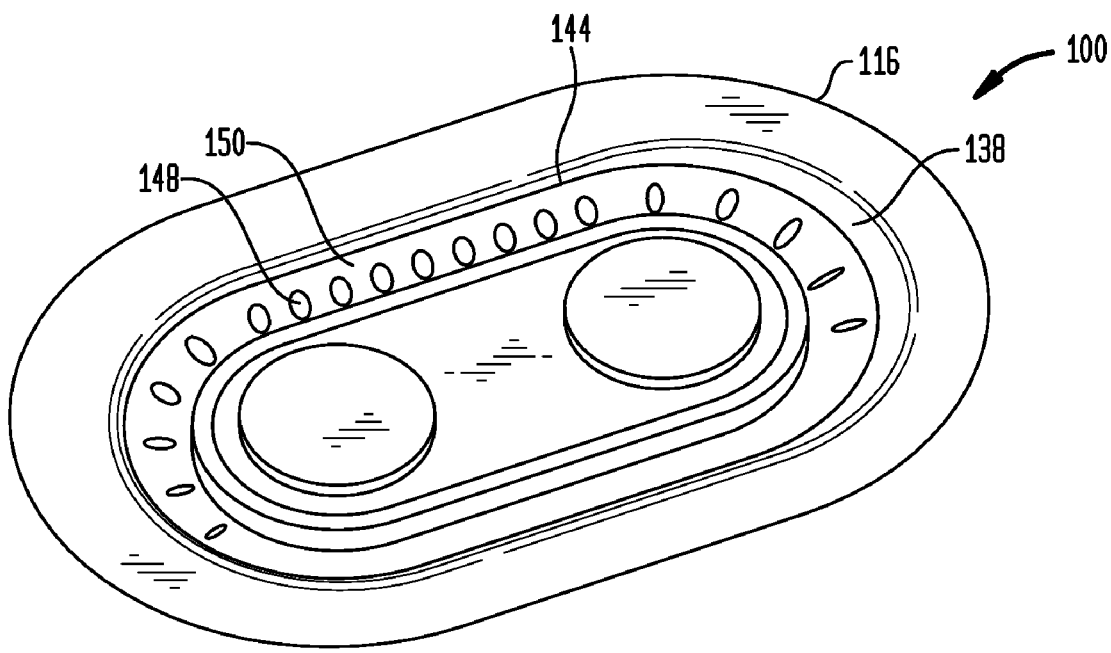
FIG. 8B shows a bottom view of a nerve stimulation patch, in accordance with one embodiment of the present invention.

Referring to FIGS. 8A and 8B, the selective nerve stimulation patch 100 desirably includes a support flange 144 that surrounds the circuitized substrate 102. The support flange 140 preferably has a sloping top surface 146 that is adapted to support the sloped transition region 138 of the top cover 116 (FIG. 7A). In one embodiment, the support flange 144 is flexible. The support flange 140 desirably has a plurality of vent openings 148 that extend between the sloping top surface 146 and the bottom surface 150 thereof. The vent openings 148 desirably enable moisture (e.g. perspiration) to escape from the patch 100. Referring to FIG. 8A, the support flange 144 may also function as a mold for controlling and shaping encapsulating material introduced over the top surface of the substrate 102. The support flange may control and limit the flow of the encapsulation material until the encapsulation material is cured. When the encapsulating material is cured, it protects the components overlying the substrate.

Referring the FIG. 8B, the support flange 144 is assembled with an underside of the top cover 116 so that it is aligned with the sloped transition region 138 of the top cover 116. The support flange 144 surrounds the circuitized substrate 102 and couples the circuitized substrate with the top cover 116. The support flange is preferably positioned between the plateau and the outer periphery of the top cover 116.

Figure 9A:
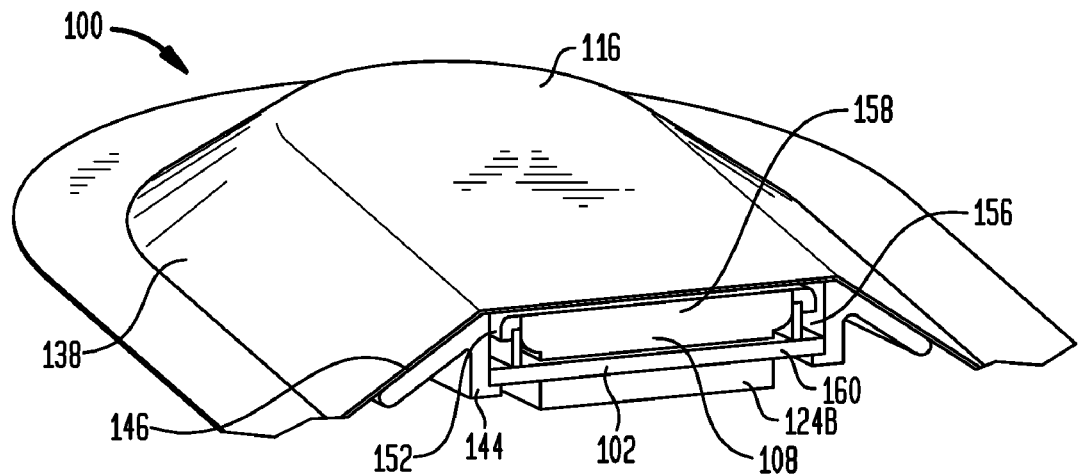
FIG. 9A shows a cross-section view of a nerve stimulation patch, in accordance with one embodiment of the present invention.
Figure 9B:
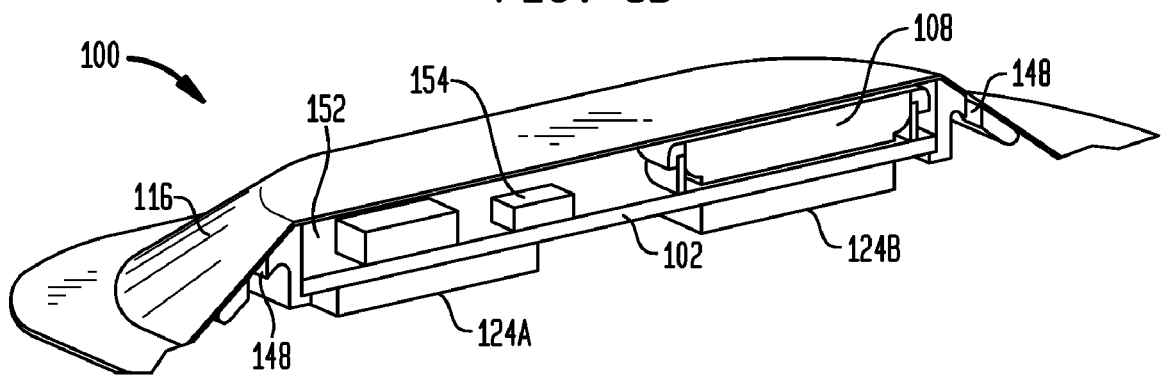
FIG. 9B shows another cross-sectional view of the nerve stimulation patch shown in FIG. 8A.

FIGS. 9A and 9B show cross-sectional views of a selective nerve stimulation patch 100, in accordance with one preferred embodiment of the present invention. The patch 100 includes the circuitized substrate 102 that is surrounded by the support flange 144 that extends around the periphery of the substrate 102. In one embodiment, the support flange 144 serves as a mold for an encapsulant material 152 that covers the components 154 overlying the top surface of the substrate 102. The encapsulant material 152 is preferably a dielectric material such as an epoxy. The encapsulant material may be transparent so as to allow optical signals to pass into and out of the encapsulant layer. The support flange 144 has a sloping top surface 146 that supports the sloped transition region 138 of the top cover 116. The patch also desirably includes the power source 108, a power source holder 156, and a power source cover 158. In one embodiment of the present invention, a second battery contact 160 may be provided atop the substrate 102 and a gap 162 may initially exist between the bottom surface of the power source 108 and the second battery contact 160. In this embodiment, the power source 108 may be depressed toward the second battery contact 160 to activate the nerve stimulation patch 100.

Referring to FIG. 9B, the support flange 144 desirably has vents 148 extending therethrough for venting moisture from the patch. The top cover 116 is preferably made of a breathable material that allows the moisture passing through the vents 148 to escape from the patch. The patch preferably includes a first conductive, adhesive pad 124A overlying a first electrode accessible at the bottom surface of the substrate 102 and a second conductive, adhesive pad 124B overlying a second electrode accessible at the bottom surface of the substrate 102. The first and second conductive pads 124A, 124B preferably form a reliable electrical interconnection between the electrodes and a patient's skin. The adhesive, conductive patches 124A, 124B may include adhesive hydrogel patches.

Figure 10:
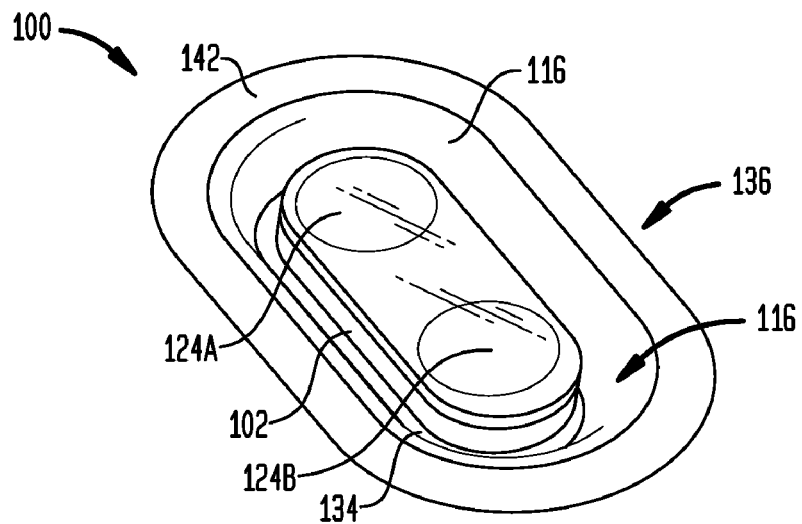
FIG. 10 shows an underside view of a nerve stimulation patch, in accordance with one embodiment of the present invention.

FIG. 10 shows the underside of the nerve stimulation patch 100 shown in FIGS. 9A and 9B, with the support flange removed. The circuit board 102 is adhered to the underside of the plateau region of the top cover 116 using the first adhesive layer 134. The second adhesive layer 142 overlies the underside, peripheral edge 136 of the top cover for attaching the top cover to a surface such as a patient's skin surface. The patch includes the conductive, adhesive pads 124A, 124B that cover the respective electrodes (not shown) for forming reliable electrical interconnections between the electrodes and the patient's skin, and for attaching the patch to a surface.

As indicated above, it is known that nerve stimulating patches can be used to stimulate both nerves and muscles within the body. One problem with conventional nerve stimulating patches is that the applied electrical signals tend to spread widely, affecting untargeted muscles and nerves as well as targeted ones. Further, to account for this signal dissipation, the applied current levels must be significantly increased to ensure adequate current densities at the targeted site. Another challenge associated with the application of electrical signals is that many nerves are stimulated by a low frequency signal, on the order of 10-40 Hz. Such a low frequency signal, however, cannot pass through body tissue to reach the target nerve(s). Many of these challenges have been overcome by the present invention, which will now be described in further detail below.

In one embodiment of the present invention, the selective nerve stimulation patch uses a pseudo-sine, an amplitude modulated waveform at 219 KHz, with the envelope width and repetition rate adjustable from 200 ms and 20 Hz respectively. The output amplitude is desirably set to 2.5 to 10 volts, eight steps of approximately one (1) volt, using an optical link to the serial port. The output voltage may be set by the user, with the use of a controller that links to the patch optically via an encoded infrared signal.

In one embodiment of the present invention, most of the waveform parameters of the stimulus output are preset, and the stimulus electrodes are located directly below the rest of the components. The patch preferably has a one-time activation switch that powers up the circuitry. Once activated, the selective nerve stimulation patch is adapted to operate continuously until the battery is depleted. The electrodes are preferably integrated into the circuitized substrate and may be gold-plated or covered by a noble metal layer than does not rapidly oxidize. The patch includes a waterproof, breathable top cover to prevent build-up of moisture inside the patch and around the electrodes, and to prevent entry of water during bathing or showering. In one embodiment, a photodiode is provided under a section of the top cover, and is used as a low-power communication receiver.

In one embodiment of the present invention, the selective nerve stimulation patch disclosed herein is adapted to be attached to the skin using self-adhesive hydrogel electrodes and a band of perimeter adhesive on the edge of the flexible top cover. Use of a self-adhesive hydrogel may eliminate the need to have a separate adhesive to hold the electrodes in place. These dual-purpose types of adhesive materials are relatively tolerant of changes in moisture and effectively attach the electrodes to the skin for long periods of time. The interface between the selective nerve stimulation patch and the skin may require the use of a water based, relatively non-compressible electrolyte material that can be a semi-liquid hydrogel, such as those used in EGG electrodes, or a semi-solid hydrogel, such as those used in TENS electrodes. In one embodiment, the hydrogel on the electrodes is configured as columns, and they are centered over electrodes (e.g. gold plated contacts) on the circuit board. The diameter of the columns determines the effective contact area of the stimulation electrodes. In one embodiment, the hydrogel columns are substantially similar in size to the electrode areas on the circuit board, but large enough to cover the metallic contacts. In one embodiment, the nerve stimulating patch has two 0.420" diameter gold plated contacts having respective centers that are one inch apart.

In one preferred embodiment of the present invention, the hydrogel pads have some thickness, which aides in breathability, shelf-life and conformation to local surface topography. As is well-known by those skilled in the art, the hydrogel pads cannot be too thick, because excessive thickness may increase the possibility of gel squeeze-out and/or increase the overall height of the device. Since a lower profile for the patch is preferred, the hydrogel should be as thin as possible. In one embodiment, the gel is approximately 0.60" thick. In one embodiment, the gap between the nearest edges of the two contacts is 0.525", thereby providing a space wide enough to resist salt bridging caused by perspiration. In one embodiment of the present invention, the electrodes are placed side by side. In another embodiment, the electrodes are concentric.

During use, the hydrogel pads may be replaced by the patient, if the patch becomes loose. Moreover, the user may use the device only some of the time. In one embodiment, the patch may be removed and later repositioned or placed back onto a surface.

The selective nerve stimulation patch of the present invention is designed to be stored for prolonged periods before use. Thus, it is essential that the patch is constructed so that there is no premature contact between the battery and the circuitry until the patch is intentionally activated. Therefore, the patch desirably has a one-time activated sealed switch mechanism. The switch mechanism may have several designs, including a reed switch that is normally "off" in the presence of a magnet (contained in the package), an over-center switch mechanism that could be mechanically toggled from a normally-off to a normally-on state, a switch like that described above where initial contact is maintained by a conductive adhesive, or a battery contact arrangement that prevents normal circuit completion until intentionally pressed by the end user.

In one embodiment of the present invention, the patch is activated by squeezing down on a battery, which causes it to shift down 0.005-0.010" in an annular battery holder so as to make permanent contact with a contact positioned on the top surface of a circuit board, thereby activating or "powering up" the device. The activation of the patch is preferably a one-time, non-reversible step that activates the circuitry, causing it to operate until the battery is depleted, at which time the nerve stimulating patch is no longer functional.

One problem with prior art nerve stimulating patches is that an edge of the patch may be snagged on another object, which may result in the patch being pulled off the patient. In order to avoid these problems, the present invention provides a sloping transition from the skin to the full thickness of the patch, thereby providing a patch that is less likely to snag onto clothing or an opposing object. In one embodiment, the patch includes a flexible, transitional support flange that fits snugly around the perimeter of the circuitized substrate, creating a sloped transition to the skin. Vent holes or perforations extend through the support flange to provide an escape route for trapped moisture through the breathable top cover. The support flange performs several functions including providing a soft, no-pinch edge for the patch, creating a snag-resistant, sloped perimeter that also supports the top cover where it transitions from the top plateau surface of the patch to the skin, and it provides an integral, low-profile enclosure for containing an encapsulant material that encapsulates and protects the electronics from moisture and corrosion during long-term storage and later use.

In one embodiment of the present invention, the encapsulation material is a semi-rigid epoxy, which is transparent or translucent to permit light from the LED to be seen and for IR optical signals from an external controller to reach the photodiode. In one embodiment, the flexible top cover material allows IR or visible light to pass therethrough. In another embodiment, the top cover has holes formed therein that enable light to pass through for reaching the optical components described herein.

In one or more embodiments of the present invention, a selective nerve stimulation patch is adapted to generate a modulated waveform for stimulating a target nerve using the devices and techniques described in commonly assigned United States Patent Application Publication Nos. US 2005/0277998 (U.S. application Ser. No. 11/146,522, filed Jun. 7, 2005), and US 2006/0195153 (U.S. application Ser. No. 11/343,627, filed Jan. 31, 2006), the disclosures of which are hereby incorporated by reference herein. The waveform is desirably generated by modulating a carrier waveform with a pulse envelope. Properties of the carrier waveform such as amplitude, frequency, and the like, are chosen so as to overcome the tissue impedance and the stimulation threshold of the target nerve. The pulse envelope is a waveform having a specific pulse width, amplitude and shape designed to selectively stimulate the target nerve. This waveform is able to penetrate efficiently through the tissue to reach the target nerve with minimal loss in the strength of the electrical signal, thereby saving battery power that would otherwise have been used in several attempts to stimulate the target nerve with low frequency signals. Moreover, only the target nerve is stimulated, and non-target nerves are not stimulated.

Figure 11:
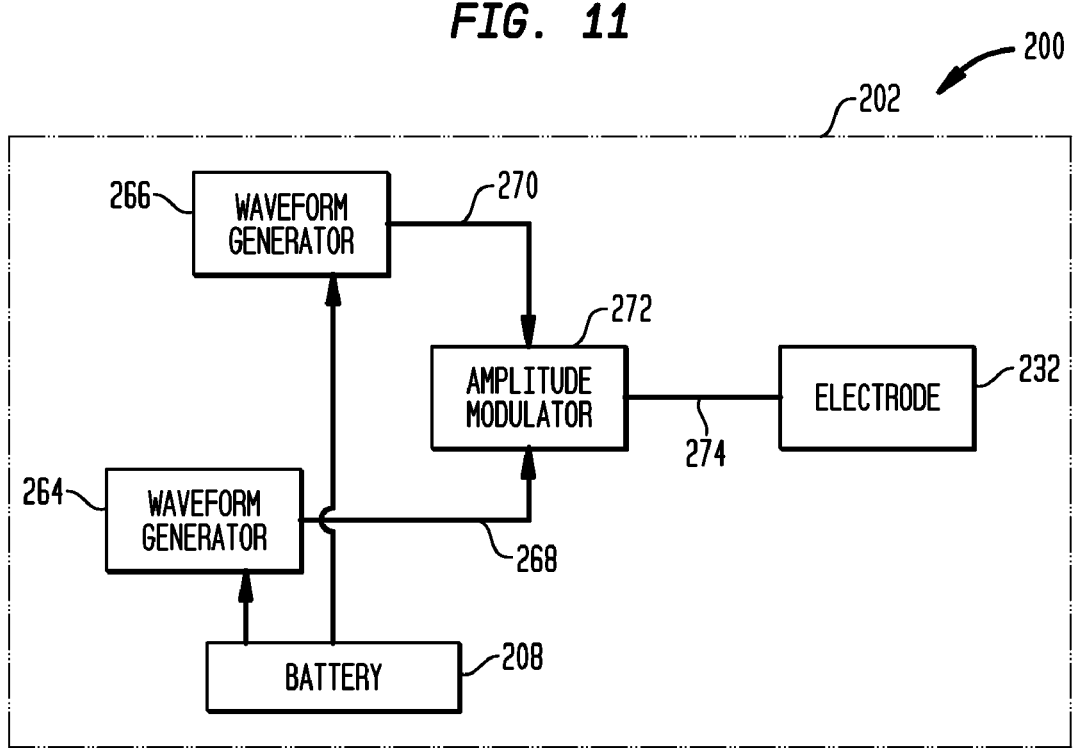
FIG. 11 shows a nerve stimulation patch, in accordance with yet another embodiment of the present invention.

Referring to FIG. 11, in one embodiment of the present invention, a selective nerve stimulation patch 200 includes a circuitized substrate 202 that may be operated to generate electrical signals for stimulating nerves and body parts. The patch 100 includes a suitable power source 208, such as a lithium battery, a first waveform generator 264, and a second waveform generator 266. The first and second waveform generators 264, 266 are electrically coupled to and powered by the battery 208. The waveform generators 264, 266 may be of any suitable type, such as those sold by Texas Instruments of Dallas, Tex. under model number NE555. The first waveform generator 264 generates a first waveform 268 having a frequency known to stimulate nerves in the body. In one embodiment, the frequency is within the range of about 10-30 Hz. In another embodiment, the frequency is within the range of about 10-40 Hz. As noted above, such low frequency signals (e.g. 10-40 Hz.) cannot, in and of themselves, pass through body tissue to effectively stimulate target nerves. In order to overcome these problems, the nerve stimulating patch 200 of the present invention may include the second waveform generator 266 that generates a second waveform 270 having a higher frequency. The second waveform has a frequency of approximately 10-400 KHz. The second waveform 270 is applied along with the first waveform 268 to an amplitude modulator 272, such as the modulator having the designation On-Semi MC1496, which is sold by Texas Instruments.

Figure 12:
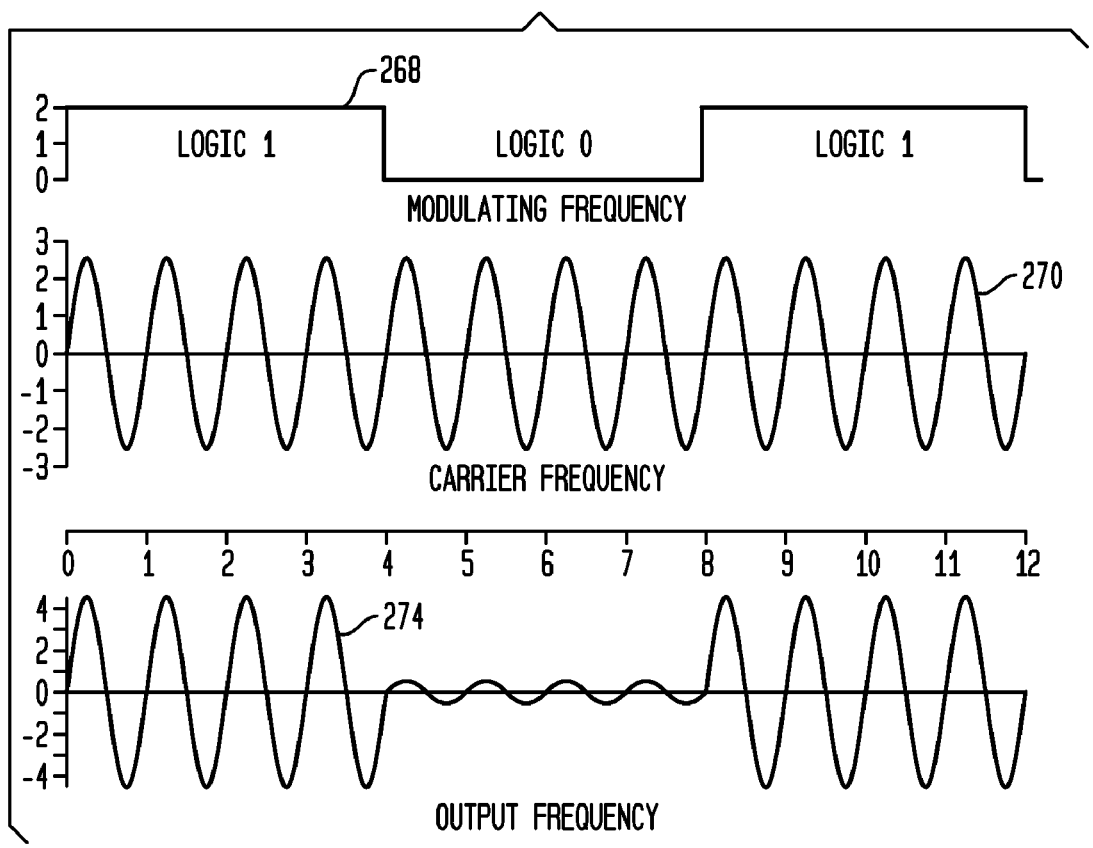
FIG. 12 shows exemplary waveforms generated by the nerve stimulation patch shown in FIG. 11.

The modulator 272 generates a modulated waveform 274 that is transmitted to electrodes 232 accessible at a bottom surface of the circuitized substrate 202. Although FIG. 11 shows only one electrode 232, preferred embodiments of the present invention may have two or more electrodes. The electrodes 232, in turn, apply the modulated waveform 274 to a target nerve to stimulate the target nerve. Referring to FIGS. 11 and 12, the first waveform 268 is preferably a square wave having a frequency of approximately 10-40 Hz, and the second waveform 270 is preferably a sinusoidal signal having a frequency in the range of 10-400 KHz. The above-listed frequency ranges are merely exemplary so that other frequency ranges may be utilized and still fall within the scope of the present invention. As those skilled in the art will readily recognize, modulation of the first waveform 268 with the second waveform (carrier wave) 270 results in a modulated waveform or signal 274 having the configuration shown in FIG. 12.

In one embodiment of the present invention, the electrodes are adapted to apply modulated waveform signals to one or more target nerves (not shown) associated with a selected body part (e.g. the bladder). The modulated waveform includes the high frequency carrier waveform that is capable of easily propagating through the body tissue and the low frequency signal that is adapted to stimulate the target nerve (s) for the selected body part. Referring to FIG. 12, although the present invention is not limited by any particular theory of operation, it is believed that generating a modulated signal 274 enables transmission of the nerve stimulating waveform 268 through tissue due to the high frequency nature of the carrier waveform 270 that effectively carries the low frequency waveform 268 to the target nerve.

In one embodiment of the present invention, an underlying principal of operation is that nerves within the body can be selectively targeted for stimulation without affecting adjacent neurons. As is well known to those skilled in the art, bioelectric potentials are produced as a result of electrochemical activity of excitable cells found within nervous system tissue. These excitable cells exist in two electrical states, resting potential or action potential. Cells remain in the resting potential state until adequate stimulus is provided to cause the cells to reach the action or threshold potential, at which time the nerve "fires," and the action potential travels at a constant conduction velocity unattenuated along the cell membranes. This all-or-nothing response of the action potential causes the cell's membrane potential to go through a characteristic repeatable cycle, where the potential first goes from the negative resting potential, to a positive action potential, and then back down to the negative resting potential again all within approximately 1 ms. The response remains the same regardless of the magnitude of the stimulus, so long as the stimulus exceeds the threshold potential.

When an excitable cell membrane has an action potential response (from an adequate stimulus), its ability to respond to a second stimulus is significantly altered. During the initial, depolarizing portion of the action potential, the cell membrane cannot respond to additional stimulus regardless of its intensity. This period is referred to as the absolute refractory period. Immediately following the absolute refractory period is a period referred to as a relative refractory period. During the relative refractory period, the cell membrane can respond only to intense stimulation. The existence of the absolute and relative refractory periods results in an upper frequency limit at which a cell can be repeatedly discharged. Thus, neurons can be seen as frequency dependent devices. The frequency dependent component of the neuron depends on its total capacitance, which will vary from neuron to neuron and will be a function of its length, diameter, coating (myelination) and the permeativity of the dielectric medium. In other words, for any given dielectric medium, varying either the length or diameter of the neuron, or its myelination, will vary its total capacitance.

Since neurons in the human body do vary greatly in diameter, length and myelination, the capacitance and conduction velocity (operating frequency) for these neurons vary as well. Using the differences in physical characteristics of adjacent neurons, selected nerves can be targeted for stimulation without affecting adjacent neurons. That is, selective neural stimulation can be achieved by characterizing the frequency response (capacitance) of adjacent neurons, and tuning the stimulation frequency to an area of no-overlap. For example, for two adjacent neurons, where neuron A has a frequency band of operation from 0-20 Hz and neuron B has a frequency band of operation from 20-30 Hz, neuron B can be selectively stimulated with no effect on neuron A. Further, neuron A can be selectively stimulated even in an overlapping frequency range if stimulation is applied during neuron B's absolute refractory period, during which no amount of stimulation will cause neuron B to fire as discussed above, or if the stimulation is less than the magnitude required to cause stimulation during the relative refractory period. As described further herein, these principles can be applied to achieve selective stimulation of two or more nerves within the body.

Figure 13:
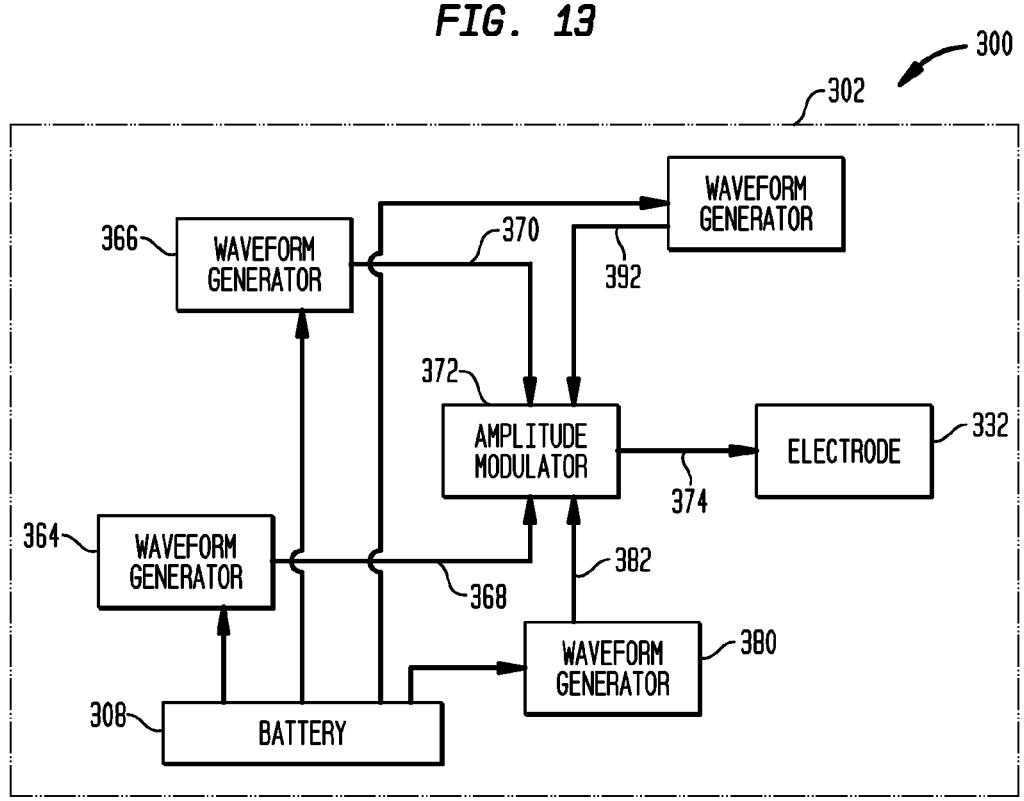
FIG. 13 shows a nerve stimulation patch, in accordance with still another embodiment of the present invention.

Referring to FIG. 13, in one embodiment of the present invention, a selective nerve stimulation patch 300 includes a circuitized substrate 302 having components provided thereon for generating electrical signals for stimulating target nerves. The nerve stimulation patch 300 includes a suitable power source 308, such as a lithium ion battery, a first waveform generator 364 that produces a first waveform 368, a second waveform generator 366 that produces a second waveform 370, and a third waveform generator 380 that produces a third waveform 382. The first, second, and third waveform generators 364, 366, and 380 are preferably electrically coupled to and powered by the battery 308. These waveform generators may be of any suitable type, such as those sold by Texas Instruments of Dallas, Tex. under model number NE555. The output of the first 364, second 366 and third 226 waveform generators are applied to amplitude modulator 372, which modulates the three waveforms into a modulated signal package 374. The term "signal package" is used herein to describe a single output signal consisting or two or more individual signals modulated together in any way.

Figure 14:
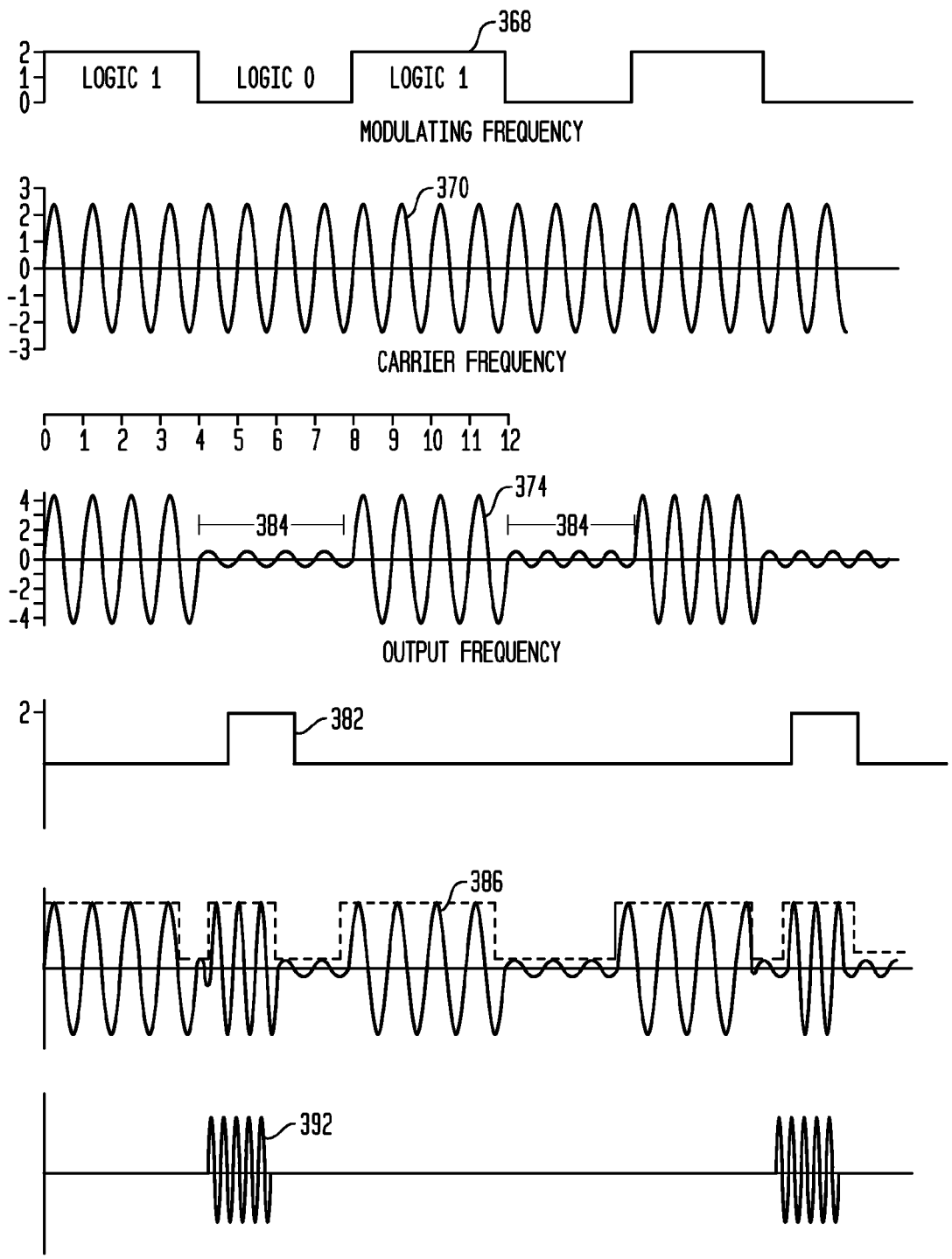
FIG. 14 shows exemplary waveforms generated by the nerve stimulation patch shown in FIG. 13.

Referring to FIGS. 13 and 14, the first waveform generator 364 generates the first waveform 368 or signal having a frequency known to stimulate a first selected body part, such as a pudendal nerve, which is known to be stimulated by a frequency approximately within the range of 10-30 Hz. As indicated above, it has been proven difficult to pass such a low frequency signal through body tissue to reach certain target nerves with sufficient current density to stimulate the target nerves. To address this problem, the second waveform generator 366 generates a higher frequency carrier waveform 370, which is applied along with the first waveform 368 to an amplitude modulator 372, such as an On-Semi MC1496 modulator sold by Texas Instruments. The first waveform 368 is preferably a square wave having a frequency of approximately 10-30 Hz, and the second waveform 370 is preferably a sinusoidal signal having a frequency in the range of 10-400 KHz. The modulation of the first waveform 368 with the second waveform (carrier waveform) 370 results in a modulated waveform or signal 374 having generally the configuration shown in FIG. 14. The signals shown in FIG. 14 are for illustrative purposes only, and are not intended as true representations of the exemplary signals described herein.

In operation, the modulated signal 374 generated by modulator 372 is transmitted to electrodes 332. In turn, the electrodes 332 apply the modulated signal 374 to the target nerve (s). As is readily understood by those skilled in the art, the use of the modulated signal 374 provides for efficient stimulation of the target nerve(s) due to the high frequency nature of the carrier waveform enabling the low frequency signal to be detected (and responded to) by the target nerve.

Referring to FIG. 14, it has been observed that the modulated signal 374 has periodic periods of inactivity 384. Rather than using the nerve stimulating patch (FIG. 13) to selectively stimulate only one target nerve, the periodic periods of inactivity 384 of the modulated signal 374 can be taken advantage of to generate a second modulated signal adapted to stimulate a second target nerve or other body part. Referring to FIGS. 13 and 14, to accomplish this, the third waveform generator 380 generates the third waveform 382 having a frequency that is different than the first waveform 368 and that is specifically selected to stimulate a second nerve or body part. An exemplary third waveform 382 is shown in FIG. 14. The third waveform 382 is desirably out of phase with the first waveform 368 to avoid interfering with the first modulated signal 374. Further, in one embodiment of the present invention, if the frequency ranges that simulate the first and second nerves overlap, the third waveform 382 can be generated or applied during the refractory period of the first nerve to ensure that the first nerve does not respond to the second modulated signal.

The first and third waveform generators 364, 380 preferably generate their respective waveforms 368, 382 out of phase with each other so that when combined with the carrier waveform 370, they appear along separate and discrete portions of the signal package 386 (FIG. 14), and each of the first and third waveforms have a frequency selected to specifically target different nerves or body portions. For example, the first waveform 368 may have a frequency of 20 Hz, which is known to have an effect on the autonomic element branches of the pudendal nerve (for affecting an overactive bladder), and the third waveform 382 may have a frequency of 10 Hz, which is known to have an effect on the somatomotor branch of the pudendal nerve (useful in treating intersticial cystitis). To the extent there is an overlap in frequency ranges, the third waveform 382 may be applied during the refractory period of the first nerve.

By the system and method described above, individual components of the modulated signal package can be used to selectively target different nerves, different nerve branches, different muscles, or selected other body parts. That is, a single nerve stimulation patch could provide stimulation signals designed to relieve multiple different symptoms such as those associated with pain management, overactive bladder, fecal incontinence, interstitial cystitis and any other pelvic floor disorder.

Those skilled in the art will recognize that the appropriate signals may be manipulated in many different ways to achieve suitable modulated signals and/or signal packages. For example, referring to FIGS. 13 and 14, in one embodiment of the present invention, a fourth waveform generator 390 may also be included that generates a fourth carrier waveform 392 having a frequency different from the second carrier waveform 370. This may be desirable if stimulation of the first and second nerve or body part will require the signal(s) to pass through different types or amounts of tissue. As illustrated, in embodiments using a single amplitude modulator, the fourth carrier waveform 392 is preferably applied only during periods of inactivity of the first waveform 368 to avoid affecting the modulated signal 374.

Figure 15:
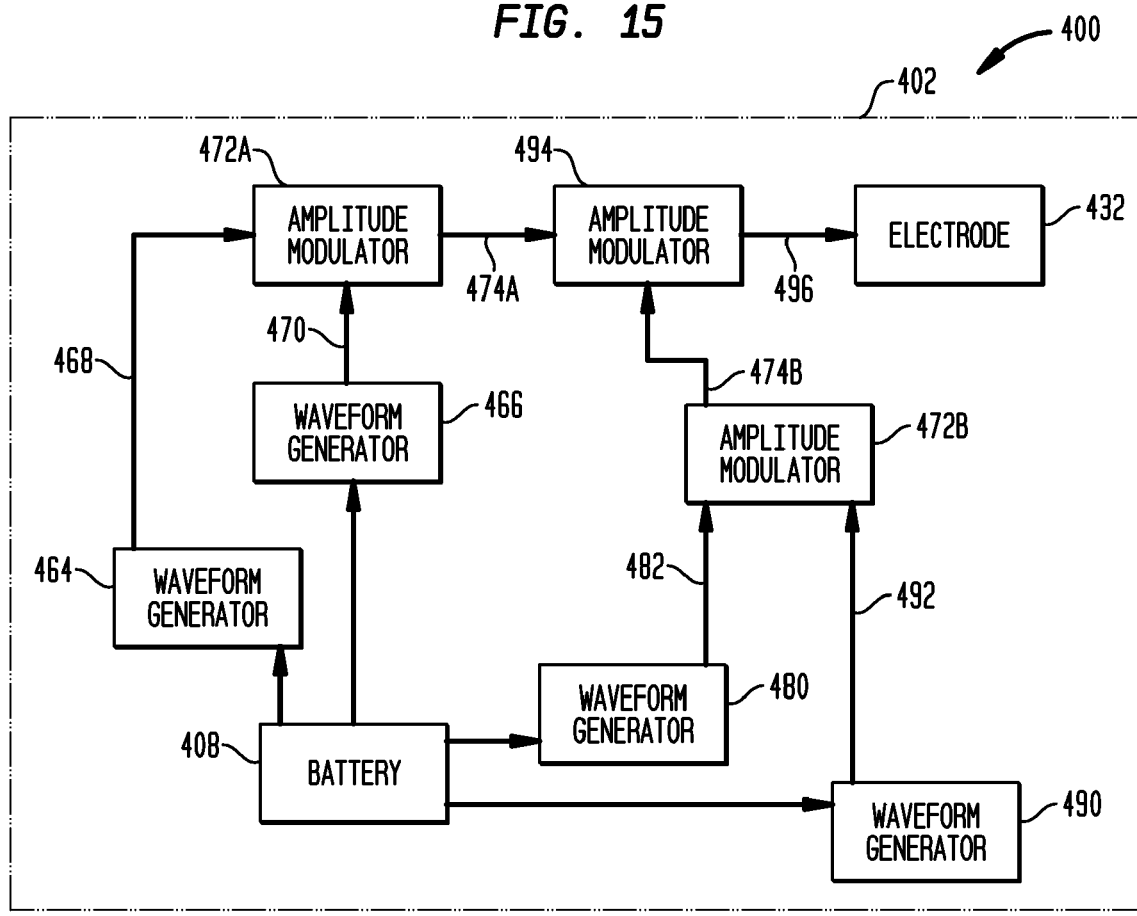
FIG. 15 shows a nerve stimulation patch, in accordance with yet another embodiment of the present invention.
Figure 16:
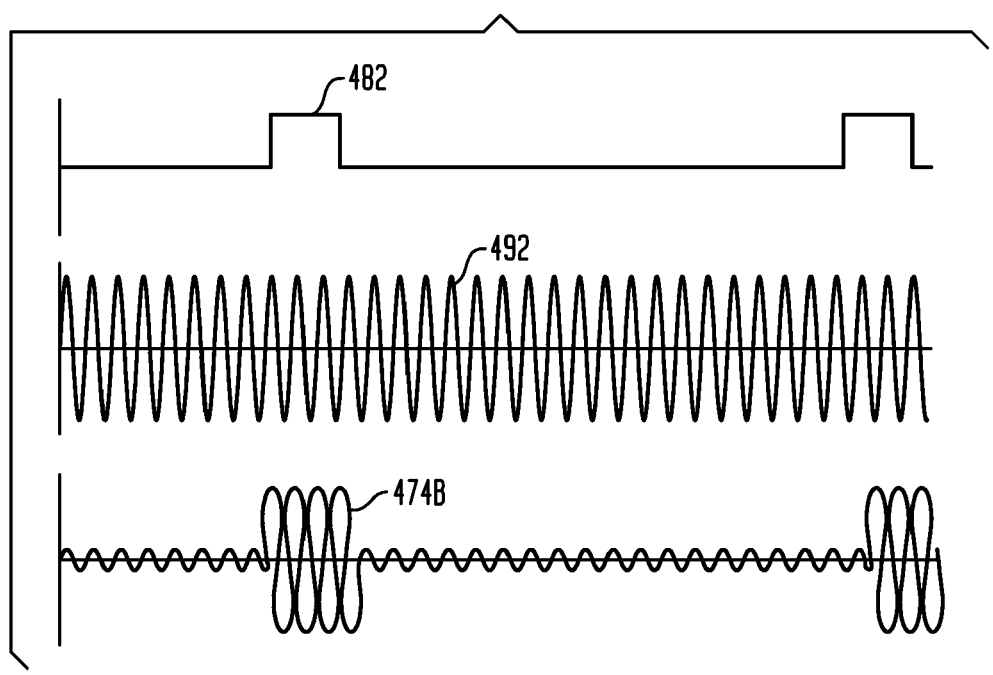
FIG. 16 shows exemplary waveforms generated by the nerve stimulation patch shown in FIG. 15.

In the embodiment of FIGS. 15 and 16, the first waveform 468 and the second carrier wave 470 may be provided to a first amplitude modulator 472A to generate a first modulated waveform 474A. The third waveform 482 and a fourth carrier waveform 492 may be provided to a second amplitude modulator 472B to generate a second modulated waveform 474B. These first and second modulated waveforms may be further modulated by a third amplitude modulator 494 to create a modulated signal package 496 that can be transmitted through electrode(s) 432.

In one embodiment of the present invention, the first and second modulated signals 474A, 474B may be applied through separate first and second electrodes (not shown). In one or more other embodiments of the present invention, when the modulated waveforms have periods of inactivity, additional signals may be inserted into these non-active periods to target other nerves, muscles, or body parts.

Referring to FIG. 17, in one embodiment of the present invention, the selective nerve stimulation patch 500 desirably has one or more biofeedback mechanisms. The biofeedback mechanisms desirably provide feedback to the system, and enable selective, as opposed to constant, operation of the system. As a result, nerve stimulation may only occur when necessary.

The patch 500 includes circuitized substrate 502, a power source 508, such as a battery, a first waveform generator 564 that generates a first waveform 568, and a second waveform generator 566 that generates a second waveform 570. The first and second waveform generators 564, 566 are electrically coupled to and powered by the battery 508. The waveform generators 564, 566 may be of any suitable type, such as those sold by Texas Instruments of Dallas, Tex. under model number NE555. The first waveform generator 564 generates a first waveform 568 having a frequency known to stimulate nerves in the body. In one embodiment, the frequency is within the range of about 10-30 Hz. In another embodiment, the frequency is within the range of about 10-40 Hz. As noted above, such low frequency signals (e.g. 10-40 Hz.) cannot, in and of themselves, pass through body tissue to effectively stimulate target nerves. In order to overcome this problem, the selective nerve stimulation patch 500 has a second waveform generator 566 that generates a second waveform 570 having a higher frequency (e.g. 10-400 KHz.) that is applied along with the first waveform 566 to an amplitude modulator 572, such as the modulator having the designation On-Semi MC1496, which is sold by Texas Instruments.

The modulator 572 generates a modulated waveform 574 that is transmitted to electrodes 532. The electrodes 532, in turn, apply the modulated waveform 574 to the target nerve (not shown) to stimulate the target nerve. In one embodiment, the selective nerve stimulation patch 500 may include a third waveform generator 580 for generating a third waveform 582, and a fourth waveform generator 590 for generating a fourth waveform 592.

The nerve stimulation patch 500 also includes one or more sensor devices 598. The sensor devices may be implantable within the body. The sensor devices 598 preferably include at least one sensor 600 that will sense a selected bio-physiological property, and a data transmission device 602 that transmits data or information gathered by the sensor 600 back outside the body to be further processed as described more fully below. The transmitter 602 may transmit the data wirelessly.

In one embodiment, the signal transmitter 602 is part of a larger signal control system 604 that further includes a receiving device 606 such as a MAX1472 from Maxim Semiconductors of Sunnyvale, Calif., that is electrically coupled to and powered by the battery 508. The receiving device 606 receives data from the one or more sensor devices 598 and provides this data to a microcontroller 608. The microcontroller is preferably programmed to receive and analyze the data, and based on this data to provide input to the first and second waveform generators 564, 566 to thereby control signal transmission by the nerve stimulation patch. The biofeedback sensor 600 may be a pressure sensor that is implanted within the body such as within the bladder. As is well known to those skilled in the art, continuously measuring the pressure within the bladder may indicate the existence and magnitude of bladder contractions. When such pressure measurements indicate spastic bladder muscle activity (as compared to normal bladder contractions which will result in a slow and steady rise of pressure within the bladder), a feedback signal can be transmitted to the receiving device 606 and subsequently to the microcontroller 608. In response to the received feedback signals, the microcontroller 608 will, via control of the waveform generators 564, 566, cause the electrode(s) 532 to transmit the modulated signal. Receipt of the modulated signal by the target nerve (e.g. the pudendal nerve) will innervate the bladder muscles to substantially eliminate the spastic muscle contractions.

In one embodiment, the biofeedback device 598 may include multiple electronic components including a power source, one or more sensor components, and an electronic interface, each of which are electrically coupled to one another and mechanically mounted on a printed circuit board in a manner well known in the art. The one or more sensor components sense predetermined physiological properties within the body, and transmit signals or data representing such properties to the electrical interface. The system may include a data storage element for storing data correlating to the sensed physiological properties, but may also include a transmitter for transmitting the data external of the patient's body so that it can be used to control generation of the modulated signal as described above. The biofeedback device may be substantially surrounded by a collapsible housing or cage.

In one preferred embodiment of the present invention, the biofeedback device preferably remains within the body (e.g. the bladder) for an extended period of time to provide constant feedback that is used to control operation of the electrode. Where constant feedback is not used, the implantable sensors described herein may nevertheless be used to obtain data useful in rendering an accurate diagnosis and/or appropriate treatment. In one embodiment of the present invention, the device may remain within the bladder for 1-2 days, with pressure measurements being taken every ½ second. The type and frequency of pressure changes can be subsequently analyzed to provide feedback to assess body function. For example, vesicle pressure measured over time can reveal voiding times and frequency, can provide an indication of an overactive bladder, or of bladder overfilling. In one embodiment, the sensor element(s) are designed to operate in an extended sleep mode, "waking up" at fixed intervals of time to measure pressure or the like. Once sufficient data has been gathered, the device can subsequently be removed from the bladder such as by inserting a catheter into the bladder to retrieve the implantable device, or using the operating channel of a cystoscope or other suitable instrument to retrieve the device. The catheter or cystoscope would be inserted into the bladder, and the device grasped and pulled back into the catheter or cystoscope channel and subsequently removed from the body.

Referring to FIG. 17, in embodiments utilizing biofeedback data, the receiver 606 may receive feedback data from more than one biofeedback device 598. In these embodiments, a second implantable biofeedback sensor similar to that shown and described above may be inserted into another body orifice (e.g. vaginal canal). The second biofeedback sensor may be encapsulated in a "tampon-like" device or casing that is made of rolled up or bound cotton, similar to a tampon. In one embodiment, the second implantable biofeedback device senses abdominal pressure, and the first implantable biofeedback device senses bladder pressure. As a result, the detrusor pressure (i.e. the pressure of the muscle lining of the wall of the bladder tissue) can be determined by subtracting the bladder pressure from the abdominal pressure. As is well known to those skilled in the art, a rise in detrusor pressure occurs when a patient strains, coughs, sneezes, laughs, etc., and detection of these pressures are clinically significant in the diagnosis of various bladder and lower urinary tract disease states. For example, the frequency of detrusor pressure increases provides meaningful data for assessing urge incontinence.

In one embodiment of the present invention, a system including a nerve stimulation patch has a first implantable biofeedback sensor and a second implantable biofeedback sensor. One of the implantable biofeedback sensors transmits data to the implantable biofeedback sensor, which then wirelessly transmits both sets of data to a receiver 606 (FIG. 17).

In one embodiment of the present invention, conductance of the stimulation energy from the electrode(s) to the target nerve or body part can be increased by the placement of a conductive tract that may extend either fully or partially from the electrode(s) to the target nerve or body part. The conductive tract may be a cross-linked polyacrylamide gel such as the Aquamid® injectable gel from Contura of Denmark. This bio-inert gel, injected or otherwise inserted, is highly conductive and may or may not be an aqueous solution. The implanted gel provides numerous benefits including ease of delivery, less invasiveness and patient comfort as the gel is not rigid and can conform to the patient's body. As stated above, the clear advantage of the injected gel tract is a highly conductive path from the electrode(s) to the target nerve that is much more conductive than the surrounding tissue. This reduces energy dispersion and increases the efficiency of the energy transfer between the electrode(s) and the target nerve.

The conductive gel extends between the electrodes and the target nerve. One advantage of using a conductive gel is that the electrodes can only come in proximity to one plane of the target nerve, whereas the deformable and flowable conductive gel can envelope the target nerve. As a result, the conductive gel can be in electrical and physical contact with the full 360 degrees of the target nerve, thereby enhancing application of the modulated waveform or nerve stimulating signals to the target nerve. In one embodiment, the conductive gel may extend from a location substantially in contact with the target nerve to a location closer to the outer skin layer. In one or more embodiments, multiple conductive gel pockets or tracts in any configuration may be used.

Although one suitable conductive gel has been described above, various others are also suitable. Many thermoset hydrogels and thermoplastic hydrogels could be used as well. Examples of thermoset hydrogels include cross-linked varieties of polyHEMA and copolymers, N-substituted acrylamides, polyvinylpyrrolidone (PVP), poly(glyceryl methacrylate), poly(ethylene oxide), poly(vinyl alcohol), poly(acrylic acid), poly(methacrylic acid), poly(N, N-dimethylaminopropyl-N'-acrylamide), and combinations thereof with hydrophilic and hydrophobic comonomers, cross-linkers and other modifiers. Examples of thermoplastic hydrogels include acrylic derivatives such as HYPAN, vinyl alcohol derivatives, hydrophilic polyurethanes (HPU) and Styrene/PVP block copolymers.

While the foregoing is directed to embodiments of the present invention, other and further embodiments of the invention may be devised without departing from the basic scope thereof.

What is claimed is:

1. A nerve stimulation patch comprising
a substrate having a top surface and a bottom surface;
components overlying the top surface of said substrate and being electrically interconnected with one another for generating at least one nerve stimulating signal;
at least one electrode disposed on said substrate and exposed at the bottom surface thereof for applying said at least nerve stimulating signal;
a waterproof, breathable top cover overlying said substrate;
a support flange surrounding said substrate and coupling said top cover with said substrate, wherein said support flange comprises top and bottom surfaces with vent openings extending therethrough, the vent openings being in communication with said top cover for venting moisture from inside said patch to outside said patch.

2. The nerve stimulation patch as claimed in claim 1, wherein said support flange has a top surface that slopes downwardly toward an outer perimeter of said support flange.

3. The nerve stimulation patch as claimed in claim 2, wherein a portion of said top cover conforms to said top surface of said support flange.

4. The nerve stimulation patch as claimed in claim 1, wherein said vent openings comprise passages fully enclosed by said support flange.

5. The nerve stimulation patch as claimed in claim 1, further comprising an encapsulant at least partially covering said components and said top surface of said substrate, wherein said support flange surrounds said encapsulant.

6. The nerve stimulation patch as claimed in claim 5, wherein said encapsulant is transparent.

7. The nerve stimulation patch as claimed in claim 6, wherein said top cover overlies said encapsulant and said top cover is at least partially translucent.

8. The nerve stimulation patch as claimed in claim 1, wherein said components overlying said substrate comprise a power source and a switch coupled with said power source for activating said patch.

9. The nerve stimulation patch as claimed in claim 8, wherein said switch comprises a switch adapted to be activated only one-time.

10. The nerve stimulation patch as claimed in claim 1, wherein one of said components comprises a light emitting element for generating light signals indicating that said patch is activated.

11. The nerve stimulation patch as claimed in claim 1, wherein one of said components comprises an optical sensor adapted to receive signals for controlling, parameters associated with said at least one nerve stimulating signal.

12. The nerve stimulation patch as claimed in claim 1, wherein said components comprise:
a first waveform generator overlying said top surface of said substrate and being adapted to generate a first waveform having a first frequency;
a second waveform generator adapted to generate a carrier waveform having a second frequency that is higher than said first frequency; and
a modulator electrically coupled to said first and second waveform generators and adapted to modulate said first waveform and said carrier waveform to generate a modulated waveform, wherein said at least one electrode is electrically coupled to said modulator for applying said modulated waveform.

13. The nerve stimulation patch as claimed in claim 12, wherein said components further comprise:
a third waveform generator adapted to generate a third waveform having a third frequency that is different from and out of phase with said first waveform;
said modulator being, electrically coupled with said third waveform generator and being, adapted to modulate said carrier, first and third waveforms to generate said modulated waveform, and wherein said first waveform is adapted to stimulate a first target nerve and said third waveform is adapted to stimulate a second target nerve.

14. A nerve stimulation patch comprising:
a circuitized substrate having a top surface and a bottom surface;
a plurality of integrated components overlying said top surface of said circuitized substrate for generating at least one nerve stimulating signal;
a power source overlying said top surface of said circuitized substrate for energizing said integrated components;
electrodes disposed within said circuitized substrate, being accessible at said bottom surface of said circuitized substrate, and being electrically interconnected with said integrated components for applying said at least one nerve stimulating, signal;
a waterproof breathable cover overlying said circuitized substrate;
a support flange coupled with and surrounding said circuitized substrate, said support flange having a top surface that slopes downwardly toward and outer perimeter thereof, wherein said support flange has a plurality of vent openings accessible at the sloping top surface thereof that are in communication with said waterproof, breathable top cover for venting moisture from said patch.

15. The nerve stimulation patch as claimed in claim 14, further comprising conductive, adhesive pads overlying said electrodes for securing said patch to a surface.

16. The nerve stimulation patch as claimed in claim 15, wherein said conductive adhesive pads comprise adhesive hydrogel pads.

17. The nerve stimulation patch as claimed in claim 14, further comprising a transparent encapsulant material overlying said integrated components and said top surface of said substrate, said support flange surrounding said transparent encapsulant material.

18. The nerve stimulation patch as claimed in claim 14, wherein said integrated components comprise:
a first waveform generator overlying said top surface of said circuitized substrate and being adapted to generate a first waveform having a first frequency;
a second waveform generator adapted to generate a carrier waveform having a second frequency that is higher than said first frequency; and
a modulator electrically coupled to said first and second waveform generators and adapted to modulate said first waveform and said carrier waveform to generate a modulated waveform, wherein at least one of said electrodes is electrically coupled to said modulator for applying said modulation waveform.

19. A nerve stimulation patch comprising:
a substrate having a top surface and a bottom surface;
integrated components overlying said top surface of said substrate and being electrically interconnected with one another for generating at least one nerve stimulating signal;
a waterproof, breathable cover overlying said substrate and said integrated components;
a support flange surrounding said substrate and coupling said waterproof, breathable cover with said substrate, said support flange having a top surface that slopes downwardly toward an outer perimeter thereof, wherein at least a portion of said cover conforms to said sloping top surface of said support flange, wherein said support flange comprises a plurality of vents extending from an underside thereof to said sloping top surface thereof, said vents being in communication with said waterproof, breathable material for venting moisture from inside said patch to outside said patch.

20. The nerve stimulation patch as claimed in claim 19, further comprising a transparent encapsulant material overlying said integrated components, wherein said support flange surrounds said transparent encapsulant.

21. The nerve stimulation patch as claimed in claim 20, wherein said integrated components comprise a power source, a one-time activation switch, a light emitting element, and an optical sensor, and wherein said waterproof, breathable cover comprises a first opening aligned with said one-time activation switch, a second opening aligned with said light emitting element, and a third opening aligned with said optical sensor.

22. The nerve stimulation patch as claimed in claim 19, thither comprising conductive, adhesive pads covering said electrodes, and an adhesive layer covering a peripheral, underside portion of said waterproof, breathable cover for attaching said patch to a surface.

* * * * *